US012721633B2

(12) United States Patent
Hatch et al.

(10) Patent No.: US 12,721,633 B2
(45) Date of Patent: Sep. 1, 2026

(54) PIVOTABLE BONE CUTTING GUIDE USEFUL FOR BONE REALIGNMENT AND COMPRESSION TECHNIQUES

(71) Applicant: Treace Medical Concepts, Inc., Ponte Vedra, FL (US)

(72) Inventors: Daniel J. Hatch, Greeley, CO (US); Joe W. Ferguson, Ponte Vedra Beach, FL (US); Paul Dayton, Ankeny, IA (US); W. Bret Smith, Lexington, SC (US); Lowell Weil, Jr., Lake Forst, IL (US); F. Barry Bays, Collierville, TN (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

(21) Appl. No.: 18/544,406

(22) Filed: Dec. 18, 2023

(65) Prior Publication Data

US 2024/0115271 A1 Apr. 11, 2024

Related U.S. Application Data

(60) Continuation of application No. 17/106,314, filed on Nov. 30, 2020, now Pat. No. 11,844,533, which is a (Continued)

(51) Int. Cl.
*A61B 17/15* (2006.01)
*A61B 17/17* (2006.01)

(52) U.S. Cl.
CPC ........ *A61B 17/151* (2013.01); *A61B 17/1739* (2013.01); *A61B 17/1775* (2016.11)

(58) Field of Classification Search
CPC .............. A61B 17/151; A61B 17/1739; A61B 17/1775
See application file for complete search history.

(56) References Cited

U.S. PATENT DOCUMENTS 3,584,667 A 6/1971 Reiland
3,664,022 A 5/1972 Small
(Continued)

FOREIGN PATENT DOCUMENTS

AU 2009227957 B2 7/2014
CA 2491824 A1 9/2005
(Continued)

OTHER PUBLICATIONS

Lapidus, "The Author's Bunion Operation From 1931 to 1959," Clinical Orthopaedics, vol. 16, 1960, pp. 119-135.
(Continued)

*Primary Examiner* — Anu Ramana
(74) *Attorney, Agent, or Firm* — Fredrikson & Byron, P.A.

(57) ABSTRACT

Instruments and surgical techniques may be used to correct a bone deformity, such as a bunion in which a metatarsal is misaligned with respect to a medial cuneiform. In some examples, a bone cutting guide is utilized to cut an end of the metatarsal and/or an end of the medial cuneiform to facilitate realignment of the bones. The cutting guide can have a pivotable cut guide surface along which a cutting instrument is translated to provide a precise bone cut. In some applications, after suitably preparing and aligning the bones, the bones are compressed together using a fixation pin. The fixation pin can be driven through one of the bones, into the second bone, and then further driven to compress the bones together.

30 Claims, 21 Drawing Sheets

Related U.S. Application Data division of application No. 15/047,288, filed on Feb. 18, 2016, now Pat. No. 10,849,631.

(60) Provisional application No. 62/117,747, filed on Feb. 18, 2015.

(56) References Cited

U.S. PATENT DOCUMENTS 3,835,858 A 9/1974 Hagen
4,069,824 A 1/1978 Weinstock
4,159,716 A 7/1979 Borchers
4,187,840 A 2/1980 Watanabe
4,335,715 A 6/1982 Kirkley
4,338,927 A 7/1982 Volkov et al.
4,349,018 A 9/1982 Chambers
4,364,381 A 12/1982 Sher et al.
4,409,973 A 10/1983 Neufeld
4,440,168 A 4/1984 Warren
4,475,544 A 10/1984 Reis
4,501,268 A 2/1985 Comparetto
4,502,474 A 3/1985 Comparetto
4,509,511 A 4/1985 Neufeld
4,565,191 A 1/1986 Slocum
4,570,624 A 2/1986 Wu
4,627,425 A 12/1986 Reese
4,628,919 A 12/1986 Clyburn
4,632,102 A 12/1986 Comparetto
4,664,102 A 5/1987 Comparetto
4,708,133 A 11/1987 Comparetto
4,736,737 A 4/1988 Fargie et al.
4,750,481 A 6/1988 Reese
4,754,746 A 7/1988 Cox
4,757,810 A 7/1988 Reese
4,895,141 A 1/1990 Koeneman et al.
4,952,214 A 8/1990 Comparetto
4,959,066 A 9/1990 Dunn et al.
4,978,347 A 12/1990 Ilizarov
4,988,349 A 1/1991 Pennig
4,995,875 A 2/1991 Coes
5,021,056 A 6/1991 Hofmann et al.
5,035,698 A 7/1991 Comparetto
5,042,983 A 8/1991 Rayhack
5,049,149 A 9/1991 Schmidt
5,053,039 A 10/1991 Hofmann et al.
5,078,719 A 1/1992 Schreiber
5,112,334 A 5/1992 Alchermes et al.
5,122,140 A 6/1992 Asche et al.
5,122,145 A 6/1992 Fishbane
5,147,364 A 9/1992 Comparetto
5,152,280 A 10/1992 Danieli
5,176,685 A 1/1993 Rayhack
5,207,676 A 5/1993 Canadell et al.
5,246,444 A 9/1993 Schreiber
5,254,119 A 10/1993 Schreiber
5,304,177 A 4/1994 Pennig
5,312,412 A 5/1994 Whipple
5,350,382 A 9/1994 Armstrong
5,358,504 A 10/1994 Paley et al.
5,364,402 A 11/1994 Mumme et al.
5,374,271 A 12/1994 Hwang
5,413,579 A 5/1995 Du
5,417,694 A 5/1995 Marik et al.
5,449,360 A 9/1995 Schreiber
5,470,335 A 11/1995 Du Toit
5,490,854 A 2/1996 Fisher et al.
5,529,075 A 6/1996 Clark
5,540,695 A 7/1996 Levy
5,578,038 A 11/1996 Slocum
5,586,564 A 12/1996 Barrett et al.
5,601,565 A 2/1997 Huebner
5,613,969 A 3/1997 Jenkins, Jr.
5,620,442 A 4/1997 Bailey et al.
5,620,448 A 4/1997 Puddu
5,643,270 A 7/1997 Combs
5,667,510 A 9/1997 Combs
5,702,389 A 12/1997 Taylor et al.
H1706 H 1/1998 Mason
5,722,978 A 3/1998 Jenkins, Jr.
5,749,875 A 5/1998 Puddu
5,779,709 A 7/1998 Harris, Jr. et al.
5,788,695 A 8/1998 Richardson
5,803,924 A 9/1998 Oni et al.
5,810,822 A 9/1998 Mortier
5,843,085 A 12/1998 Graser
5,893,553 A 4/1999 Pinkous
5,911,724 A 6/1999 Wehrli
5,935,128 A 8/1999 Carter et al.
5,941,877 A 8/1999 Viegas et al.
5,947,973 A 9/1999 Masini
5,951,556 A 9/1999 Faccioli et al.
5,980,526 A 11/1999 Johnson et al.
5,984,931 A 11/1999 Greenfield
6,007,535 A 12/1999 Rayhack et al.
6,027,504 A 2/2000 Mcguire
6,030,391 A 2/2000 Brainard et al.
6,162,223 A 12/2000 Orsak et al.
6,171,309 B1 1/2001 Huebner
6,203,545 B1 3/2001 Stoffella
6,248,109 B1 6/2001 Stoffella
6,391,031 B1 5/2002 Toomey
6,478,799 B1 11/2002 Williamson
6,511,481 B2 1/2003 Von Hoffmann et al.
6,547,793 B1 4/2003 Mcguire
6,676,662 B1 1/2004 Bagga et al.
6,719,773 B1 4/2004 Boucher et al.
6,743,233 B1 6/2004 Baldwin et al.
6,755,838 B2 6/2004 Trnka
6,796,986 B2 9/2004 Duffner
6,859,661 B2 2/2005 Tuke
7,018,383 B2 3/2006 Mcguire
7,033,361 B2 4/2006 Collazo
7,097,647 B2 8/2006 Segler
7,112,204 B2 9/2006 Justin et al.
7,153,310 B2 12/2006 Ralph et al.
7,182,766 B1 2/2007 Mogul
7,241,298 B2 7/2007 Nemec et al.
7,282,054 B2 10/2007 Steffensmeier et al.
7,377,924 B2 5/2008 Raistrick et al.
7,465,303 B2 12/2008 Riccione et al.
7,540,874 B2 6/2009 Trumble et al.
7,572,258 B2 8/2009 Stiernborg
7,635,365 B2 12/2009 Ellis et al.
7,641,660 B2 1/2010 Lakin et al.
D610,257 S 2/2010 Horton
7,686,811 B2 3/2010 Byrd et al.
7,691,108 B2 4/2010 Lavallee
7,763,026 B2 7/2010 Egger et al.
D629,900 S 12/2010 Fisher
7,967,823 B2 6/2011 Ammann et al.
7,972,338 B2 7/2011 O'Brien
D646,389 S 10/2011 Claypool et al.
8,057,478 B2 11/2011 Kuczynski et al.
8,062,301 B2 11/2011 Ammann et al.
D651,315 S 12/2011 Bertoni et al.
D651,316 S 12/2011 May et al.
8,080,010 B2 12/2011 Schulz et al.
8,080,045 B2 12/2011 Wotton, III
8,083,746 B2 12/2011 Novak
8,123,753 B2 2/2012 Poncet
8,137,406 B2 3/2012 Novak et al.
8,147,530 B2 4/2012 Strnad et al.
8,167,918 B2 5/2012 Strnad et al.
8,172,848 B2 5/2012 Tomko et al.
8,192,441 B2 6/2012 Collazo
8,197,487 B2 6/2012 Poncet et al.
8,231,623 B1 7/2012 Jordan
8,231,663 B2 7/2012 Kay et al.
8,236,000 B2 8/2012 Ammann et al.
8,246,561 B1 8/2012 Agee et al.
D666,721 S 9/2012 Wright et al.
8,262,664 B2 9/2012 Justin et al.
8,277,459 B2 10/2012 Sand et al.
8,282,644 B2 10/2012 Edwards
8,282,645 B2 10/2012 Lawrence et al.

(56) References Cited

U.S. PATENT DOCUMENTS 8,292,966 B2 10/2012 Morton
8,303,596 B2 11/2012 Plaky et al.
8,313,492 B2 11/2012 Wong et al.
8,323,289 B2 12/2012 Re
8,328,806 B2 12/2012 Tyber et al.
8,337,503 B2 12/2012 Lian
8,343,159 B2 1/2013 Bennett
8,377,105 B2 2/2013 Bscher
D679,395 S 4/2013 Wright et al.
8,409,209 B2 4/2013 Ammann et al.
8,435,246 B2 5/2013 Fisher et al.
8,475,462 B2 7/2013 Thomas et al.
8,496,662 B2 7/2013 Novak et al.
8,518,045 B2 8/2013 Szanto
8,523,870 B2 9/2013 Green, II et al.
8,529,571 B2 9/2013 Horan et al.
8,540,777 B2 9/2013 Ammann et al.
8,545,508 B2 10/2013 Collazo
D694,884 S 12/2013 Mooradian et al.
D695,402 S 12/2013 Dacosta et al.
8,652,142 B2 2/2014 Geissler
8,657,820 B2 2/2014 Kubiak et al.
D701,303 S 3/2014 Cook
8,672,945 B2 3/2014 Lavallee et al.
8,696,716 B2 4/2014 Kartalian et al.
8,702,715 B2 4/2014 Ammann et al.
D705,929 S 5/2014 Frey
8,715,363 B2 5/2014 Ratron et al.
8,728,084 B2 5/2014 Berelsman et al.
8,758,354 B2 6/2014 Habegger et al.
8,764,760 B2 7/2014 Metzger et al.
8,764,763 B2 7/2014 Wong et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,795,286 B2 8/2014 Sand et al.
8,801,727 B2 8/2014 Chan et al.
8,808,303 B2 8/2014 Stemniski et al.
8,828,012 B2 9/2014 May et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
D720,456 S 12/2014 Dacosta et al.
8,900,247 B2 12/2014 Tseng et al.
8,906,026 B2 12/2014 Ammann et al.
8,945,132 B2 2/2015 Play et al.
8,979,926 B2 3/2015 Quinn et al.
8,998,903 B2 4/2015 Price et al.
8,998,904 B2 4/2015 Zeetser et al.
9,011,507 B2 4/2015 Schelling
9,023,052 B2 5/2015 Lietz et al.
9,044,250 B2 6/2015 Olsen et al.
9,060,822 B2 6/2015 Wright et al.
9,089,376 B2 7/2015 Medoff et al.
9,101,421 B2 8/2015 Blacklidge
9,107,715 B2 8/2015 Blitz et al.
9,113,920 B2 8/2015 Ammann et al.
D740,424 S 10/2015 Dacosta et al.
9,220,518 B2 12/2015 Neal et al.
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,452,057 B2 9/2016 Dacosta et al.
9,522,023 B2 12/2016 Haddad et al.
9,592,084 B2 3/2017 Grant
9,750,538 B2 9/2017 Soffiatti et al.
9,785,747 B2 10/2017 Geebelen
9,980,760 B2 5/2018 Dacosta et al.
10,028,750 B2 7/2018 Rose
10,064,631 B2 9/2018 Dacosta et al.
10,159,499 B2 12/2018 Dacosta et al.
10,292,713 B2 * 5/2019 Fallin .................. A61B 17/151
10,327,829 B2 6/2019 Dacosta et al.
10,376,268 B2 8/2019 Fallin et al.
10,470,779 B2 11/2019 Fallin et al.
10,575,862 B2 * 3/2020 Bays .................. A61B 17/1775
10,729,453 B2 * 8/2020 Woodard ............. A61B 17/151
10,779,867 B2 9/2020 Penzimer et al.
11,116,558 B2 * 9/2021 Smith ............... A61B 17/8866
11,304,705 B2 4/2022 Fallin et al.
11,304,735 B2 * 4/2022 Sayger ............... A61B 17/8866
11,931,106 B2 * 3/2024 Perler .................. A61B 17/152
11,986,251 B2 * 5/2024 Perler ............... A61B 17/8095
2002/0058944 A1 5/2002 Michelson
2002/0099381 A1 7/2002 Maroney
2002/0107519 A1 8/2002 Dixon et al.
2002/0165552 A1 11/2002 Duffner
2002/0198531 A1 12/2002 Millard et al.
2004/0010259 A1 1/2004 Keller et al.
2004/0039394 A1 2/2004 Conti et al.
2004/0097946 A1 5/2004 Dietzel et al.
2004/0138669 A1 7/2004 Horn
2005/0004676 A1 1/2005 Schon et al.
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0228389 A1 10/2005 Stiernborg
2005/0251147 A1 11/2005 Novak
2005/0267482 A1 12/2005 Hyde
2005/0273112 A1 12/2005 Mcnamara
2006/0036257 A1 2/2006 Steffensmeier
2006/0129163 A1 6/2006 Mcguire
2006/0206044 A1 9/2006 Simon
2006/0217733 A1 9/2006 Plassky et al.
2006/0229621 A1 10/2006 Cadmus
2006/0241607 A1 10/2006 Myerson et al.
2006/0241608 A1 10/2006 Myerson et al.
2006/0247787 A1 11/2006 Rydell et al.
2006/0264961 A1 11/2006 Murray-Brown
2007/0010818 A1 1/2007 Stone et al.
2007/0123857 A1 5/2007 Deffenbaugh et al.
2007/0233138 A1 10/2007 Figueroa et al.
2007/0265634 A1 11/2007 Weinstein
2007/0276383 A1 11/2007 Rayhack
2008/0009863 A1 1/2008 Bond et al.
2008/0015603 A1 1/2008 Collazo
2008/0039850 A1 2/2008 Rowley et al.
2008/0091197 A1 4/2008 Coughlin
2008/0140081 A1 6/2008 Heavener et al.
2008/0147073 A1 6/2008 Ammann et al.
2008/0172054 A1 7/2008 Claypool et al.
2008/0195215 A1 8/2008 Morton
2008/0208252 A1 8/2008 Holmes
2008/0262500 A1 10/2008 Collazo
2008/0269908 A1 10/2008 Warburton
2008/0288004 A1 11/2008 Schendel
2009/0036893 A1 2/2009 Kartalian et al.
2009/0036931 A1 2/2009 Pech et al.
2009/0054899 A1 2/2009 Ammann et al.
2009/0093849 A1 4/2009 Grabowski
2009/0105767 A1 4/2009 Reiley
2009/0112212 A1 4/2009 Murray et al.
2009/0118733 A1 5/2009 Orsak et al.
2009/0198244 A1 8/2009 Leibel
2009/0198279 A1 8/2009 Zhang et al.
2009/0222047 A1 9/2009 Graham
2009/0254092 A1 10/2009 Albiol Llorach
2009/0254126 A1 10/2009 Orbay et al.
2009/0287309 A1 11/2009 Walch et al.
2009/0306675 A1 12/2009 Wong et al.
2010/0069910 A1 3/2010 Hasselman
2010/0121334 A1 5/2010 Couture et al.
2010/0125300 A1 * 5/2010 Blitz ................. A61B 17/8085 606/283
2010/0130981 A1 5/2010 Richards
2010/0152782 A1 6/2010 Stone et al.
2010/0168799 A1 7/2010 Schumer
2010/0185245 A1 7/2010 Paul et al.

(56) References Cited

U.S. PATENT DOCUMENTS

2010/0249779 A1 9/2010 Hotchkiss et al.
2010/0256687 A1 10/2010 Neufeld et al.
2010/0318088 A1 12/2010 Warne et al.
2010/0324556 A1 12/2010 Tyber et al.
2011/0009865 A1 1/2011 Orfaly
2011/0093084 A1 4/2011 Morton
2011/0118739 A1 5/2011 Tyber et al.
2011/0178524 A1 7/2011 Lawrence et al.
2011/0186456 A1 8/2011 Bertazzoni et al.
2011/0245835 A1 10/2011 Dodds et al.
2011/0264149 A1 10/2011 Pappalardo et al.
2011/0288550 A1 11/2011 Orbay et al.
2011/0301648 A1 12/2011 Lofthouse et al.
2012/0016426 A1 1/2012 Robinson
2012/0029575 A1 2/2012 Orsak et al.
2012/0065689 A1 3/2012 Prasad et al.
2012/0078258 A1 3/2012 Lo et al.
2012/0123420 A1 5/2012 Honiball
2012/0123484 A1 5/2012 Lietz et al.
2012/0130376 A1 5/2012 Loring et al.
2012/0130382 A1 5/2012 Iannotti et al.
2012/0130383 A1 5/2012 Budoff
2012/0184961 A1 7/2012 Johannaber
2012/0185056 A1 7/2012 Warburton
2012/0191199 A1 7/2012 Raemisch
2012/0239045 A1 9/2012 Li
2012/0253350 A1 10/2012 Anthony et al.
2012/0265301 A1 10/2012 Demers et al.
2012/0277745 A1 11/2012 Lizee
2012/0303033 A1 11/2012 Weiner et al.
2012/0330135 A1 12/2012 Millahn et al.
2013/0012949 A1 1/2013 Fallin et al.
2013/0012952 A1* 1/2013 Fallin ................ A61B 17/1714 606/96
2013/0030438 A1 1/2013 Fox
2013/0035694 A1 2/2013 Grimm et al.
2013/0085499 A1 4/2013 Lian
2013/0085502 A1 4/2013 Harrold
2013/0096563 A1 4/2013 Meade et al.
2013/0131821 A1 5/2013 Cachia
2013/0150900 A1 6/2013 Haddad et al.
2013/0150903 A1 6/2013 Vincent
2013/0158556 A1 6/2013 Jones et al.
2013/0165936 A1 6/2013 Myers
2013/0165938 A1 6/2013 Chow et al.
2013/0172942 A1 7/2013 Wright et al.
2013/0184714 A1 7/2013 Kaneyama et al.
2013/0190765 A1 7/2013 Harris et al.
2013/0190766 A1 7/2013 Harris et al.
2013/0204259 A1 8/2013 Zajac
2013/0226248 A1 8/2013 Hatch et al.
2013/0226252 A1 8/2013 Mayer
2013/0231668 A1 9/2013 Olsen et al.
2013/0237987 A1 9/2013 Graham
2013/0237989 A1 9/2013 Bonutti
2013/0267956 A1 10/2013 Terrill et al.
2013/0310836 A1 11/2013 Raub et al.
2013/0325019 A1 12/2013 Thomas et al.
2013/0325076 A1 12/2013 Palmer et al.
2013/0331845 A1 12/2013 Horan et al.
2013/0338785 A1 12/2013 Wong
2014/0005672 A1 1/2014 Edwards et al.
2014/0025127 A1 1/2014 Richter
2014/0031882 A1 1/2014 Schmuck et al.
2014/0039501 A1 2/2014 Schickendantz et al.
2014/0039561 A1 2/2014 Weiner et al.
2014/0046387 A1 2/2014 Waizenegger
2014/0074099 A1 3/2014 Vigneron et al.
2014/0074101 A1 3/2014 Collazo
2014/0094861 A1 4/2014 Fallin
2014/0094924 A1 4/2014 Hacking et al.
2014/0135775 A1 5/2014 Maxson et al.
2014/0163563 A1 6/2014 Reynolds et al.
2014/0171953 A1 6/2014 Gonzalvez et al.
2014/0180342 A1 6/2014 Lowery et al.
2014/0188139 A1 7/2014 Fallin et al.
2014/0194884 A1 7/2014 Martin et al.
2014/0194999 A1 7/2014 Orbay et al.
2014/0207144 A1 7/2014 Lee et al.
2014/0249537 A1 9/2014 Wong et al.
2014/0257308 A1 9/2014 Johannaber
2014/0257509 A1 9/2014 Dacosta et al.
2014/0276815 A1 9/2014 Riccione
2014/0276853 A1 9/2014 Long et al.
2014/0277176 A1 9/2014 Buchanan et al.
2014/0277214 A1 9/2014 Helenbolt et al.
2014/0288562 A1 9/2014 Von Zabern et al.
2014/0296995 A1 10/2014 Reiley et al.
2014/0303621 A1 10/2014 Gerold et al.
2014/0336658 A1 11/2014 Luna et al.
2014/0343555 A1 11/2014 Russi et al.
2014/0350561 A1 11/2014 Dacosta et al.
2015/0032168 A1 1/2015 Orsak et al.
2015/0045801 A1 2/2015 Axelson, Jr. et al.
2015/0045839 A1 2/2015 Dacosta et al.
2015/0051650 A1 2/2015 Verstreken et al.
2015/0057667 A1 2/2015 Ammann et al.
2015/0066094 A1 3/2015 Anderson et al.
2015/0112446 A1 4/2015 Melamed et al.
2015/0119944 A1 4/2015 Geldwert
2015/0142064 A1 5/2015 Perez et al.
2015/0150608 A1 6/2015 Sammarco
2015/0182273 A1 7/2015 Stemniski et al.
2015/0223851 A1 8/2015 Hill et al.
2015/0245858 A1 9/2015 Weiner et al.
2016/0015426 A1 1/2016 Dayton
2016/0022315 A1 1/2016 Soffiatti et al.
2016/0135858 A1 5/2016 Dacosta et al.
2016/0151165 A1 6/2016 Fallin et al.
2016/0175089 A1 6/2016 Fallin et al.
2016/0192950 A1 7/2016 Dayton et al.
2016/0192970 A1* 7/2016 Dayton .................. A61B 17/80 606/283
2016/0199076 A1 7/2016 Fallin et al.
2016/0213384 A1 7/2016 Fallin et al.
2016/0235414 A1 8/2016 Hatch et al.
2016/0242791 A1 8/2016 Fallin et al.
2016/0256204 A1 9/2016 Patel et al.
2016/0324532 A1 11/2016 Montoya et al.
2016/0338697 A1 11/2016 Biedermann et al.
2016/0354127 A1 12/2016 Lundquist et al.
2017/0042598 A1 2/2017 Santrock et al.
2017/0042599 A1 2/2017 Bays et al.
2017/0056031 A1 3/2017 Awtrey et al.
2017/0079669 A1 3/2017 Bays et al.
2017/0143511 A1 5/2017 Cachia
2017/0164989 A1 6/2017 Weiner et al.
2018/0132868 A1 5/2018 Dacosta et al.
2018/0344334 A1 12/2018 Kim et al.
2021/0077192 A1* 3/2021 Perler ................ A61B 17/1775
2021/0338450 A1* 11/2021 Hollis .................. A61B 17/848

FOREIGN PATENT DOCUMENTS

CA 2854997 A1 5/2013
CH 695846 A5 9/2006
CN 2930668 Y 8/2007
CN 201558162 U 8/2010
CN 201572172 U 9/2010
CN 201586060 U 9/2010
CN 201912210 U 8/2011
CN 101237835 B 11/2012
CN 202801773 U 3/2013
CN 103462675 A 12/2013
CN 103505276 A 1/2014
CN 203458450 U 3/2014
CN 103735306 A 4/2014
CN 102860860 B 5/2014
CN 203576647 U 5/2014
CN 104490460 A 4/2015
CN 104510523 A 4/2015
CN 104523327 A 4/2015
CN 104546102 A 4/2015
CN 204379413 U 6/2015

(56) References Cited

FOREIGN PATENT DOCUMENTS

| | | | |
|---|---|---|---|
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | B1 | 9/2000 |
| EP | 1508316 | B1 | 5/2007 |
| EP | 1897509 | B1 | 7/2009 |
| EP | 2124772 | A1 | 12/2009 |
| EP | 2124832 | B1 | 8/2012 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 2624764 | B1 | 12/2015 |
| EP | 3023068 | A2 | 5/2016 |
| FR | 2362616 | A1 | 3/1978 |
| FR | 2764183 | B1 | 11/1999 |
| FR | 2953120 | B1 | 1/2012 |
| FR | 3030221 | A1 | 6/2016 |
| GB | 231718 | A | 4/1925 |
| GB | 2154143 | A | 9/1985 |
| GB | 2154144 | A | 9/1985 |
| GB | 2334214 | B | 1/2003 |
| IN | 200904479 | P2 | 5/2010 |
| IN | 200903719 | P1 | 9/2010 |
| IN | 140DELNP2012 | A | 1/2013 |
| IN | 201302004 | P2 | 1/2013 |
| JP | 63005739 | A | 1/1988 |
| JP | H05031116 | A | 2/1993 |
| JP | 2004174265 | A | 6/2004 |
| JP | 2006158972 | A | 6/2006 |
| JP | 4134243 | B2 | 8/2008 |
| JP | 2008537498 | A | 9/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004089227 | A2 | 10/2004 |
| WO | 2008051064 | A1 | 5/2008 |
| WO | 2009029798 | A1 | 3/2009 |
| WO | 2009032101 | A2 | 3/2009 |
| WO | 2009158522 | A1 | 12/2009 |
| WO | 2011037885 | A1 | 3/2011 |
| WO | 2012004798 | A1 | 1/2012 |
| WO | 2012029008 | A1 | 3/2012 |
| WO | 2012103335 | A1 | 8/2012 |
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015105880 | A1 | 7/2015 |
| WO | 2015123270 | A1 | 8/2015 |
| WO | 2015127515 | A2 | 9/2015 |
| WO | 2016134160 | A1 | 8/2016 |

OTHER PUBLICATIONS

Hardy et al., "Observations on Hallux Valgus," The Journal of Bone and Joint Surgery, vol. 33B, No. 3, Aug. 1951,pp. 376-391.

Eustace et al., "Hallux valgus, first metatarsal pronation and collapse of the medial longitudinal arch—a radiological correlation," Skeletal Radiology, vol. 23, 1994, pp. 191-194.

Gotte, "Entwicklung eines Assistenzrobotersystems fr die Knieendoprothetik," Forschungsberichte, Technische Universitat Munchen, 165, 2002, 11 pages, including partial English Translation.

Grondal et al., "A Guide Plate for Accurate Positioning of First Metatarsophalangeal Joint during Fusion," Operative Orthopdie Und Traumatologie, vol. 16, No. 2, 2004, pp. 167-178 (Abstract Only).

"Lag Screw Target Bow," Stryker Leibinger GmbH & Co. KG, Germany 2004, 8 pages.

Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.

Garthwait, "Accu-Cut System Facilitates Enhanced Precision," Podiatry Today, vol. 18, No. 6, Jun. 2005, 6 pages.

"Hoffmann II Compact External Fixation System," Stryker, Brochure, Literature No. 5075-1-500, 2006, 12 pages.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Gregg et al., "Plantar plate repair and Weil osteotomy for metatarsophalangeal joint instability," Foot and Ankle Surgery, vol. 13, 2007, pp. 116-121.

Greiner, "The Jargon of Pedal Movements," Foot & Ankle International, vol. 28, No. 1, Jan. 2007, pp. 109-125.

"Futura Forefoot Implant Arthroplasty Products," Tornier, Inc., 2008, 14 pages.

Gerard et al., "The Modified Lapidus Procedure," Orthopedics, vol. 31, No. 3, Mar. 2008, 7 pages.

Hetherington et al., "Evaluation of surgical experience and the use of an osteotomy guide on the apical angle of an Austin osteotomy," The Foot, vol. 18, 2008, pp. 159-164.

"Hoffmann II Micro Lengthener," Stryker, Operative Technique, Literature No. 5075-2-002, 2008, 12 pages.

"Lapidus Pearls: Gaining Joint Exposure to Decrease Non-Union," Youtube, Retrieved online from <https://www.youtube.com/watch?v=-jqJyE7pj-Y>, dated Nov. 2, 2009, 3 pages.

Easley et al., "What is the Best Treatment for Hallux Valgus?," Evidence-Based Orthopaedics—The Best Answers to Clinical Questions, Chapter 73, 2009, pp. 479-491.

Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.

Fleming et al., "Results of Modified Lapidus Arthrodesis Procedure Using Medial Eminence as an Interpositional Autograft," The Journal of Foot & Ankle Surgery, vol. 50, 2011, pp. 272-275.

Le et al., "Tarsometatarsal Arthrodesis," Operative Techniques in Foot and Ankle Surgery, Section II, Chapter 40, 2011, pp. 281-285.

Giannoudis et al., "Hallux Valgus Correction," Practical Procedures in Elective Orthopaedic Surgery, Pelvis and Lower Extremity, Chapter 38, 2012, 22 pages.

(56) References Cited

OTHER PUBLICATIONS

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
"Foot and Ankle Instrument Set," Smith & Nephew, 2013, 2 pages.
Didomenico et al., "Lapidus Bunionectomy: First Metatarsal-Cuneiform Arthrodesis," McGlamrys Comprehensive Textbook of Foot and Ankle Surgery, Fourth Edition, vol. 1, Chapter 31, 2013, 24 pages.
Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Fishco, "A Straightforward Guide to the Lapidus Bunionectomy," Podiatry Today, Retrieved online from <https://www.hmpglobal-learningnetwork.com/site/podiatry/blogged/straightforward-guide-lapidus-bunionectomy>, dated Sep. 6, 2013, 5 pages.
Decarbo et al., "Locking Plates: Do They Prevent Complications?," Podiatry Today, Apr. 2014, 7 pages.
Didomenico et al., "Correction of Frontal Plane Rotation of Sesamoid Apparatus during the Lapidus Procedure: a Novel Approach," The Journal of Foot and Ankle Surgery, vol. 53, 2014, pp. 248-251.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Feilmeier et al., "Incidence of Surgical Site Infection in the Foot and Ankle with Early Exposure and Showering of Surgical Sites: a Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Fishco, "Making the Lapidus Easy," The Podiatry Institute, Update 2014, Chapter 14, 2014, pp. 91-93.
Groves, "Operative Report," St. Tammany Parish Hospital, Date of Procedure, Mar. 26, 2014, 2 pages.
"HAT-TRICK Lesser Toe Repair System, Foot and Ankle Technique Guide, Metatarsal Shortening Osteotomy Surgical Technique," Smith & Nephew, 2014, 16 pages.
"HAT-TRICK Lesser Toe Repair System," Smith & Nephew, Brochure, Aug. 2014, 12 pages.
Hirao et al., "Computer assisted planning and custom-made surgical guide for malunited pronation deformity after first metatarsophalangeal joint arthrodesis in rheumatoid arthritis: a case report," Computer Aided Surgery, vol. 19, Nos. 1-3, 2014, pp. 13-19.
Hoffmann Small System External Fixator Orthopedic Instruments, Stryker, retrieved Dec. 19, 2014, from the Internet: <http://www.alibaba.com/product-detail/Stryker-Hoffmann-Small-System-External-Fixator_1438850129.html>, 3 pages.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Fallin et al., US Provisional Application Entitled Indexed Tri-Planar Osteotomy Guide and Method, U.S. Appl. No. 62/118,378, filed Feb. 19, 2015, 62 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Groves, "Functional Position Joint Sectioning: Pre-Load Method for Lapidus Arthrodesis," The Podiatry Institute, Update 2015, Chapter 6, 2015, pp. 23-29.
Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.
International Patent Application No. PCT/US2016/018484, International Search Report and Written Opinion mailed Jun. 30, 2016, 12 pages.
Langan et al., "Maintenance of Correction of the Modified Lapidus Procedure With a First Metatarsal to Intermediate Cuneiform Cross-Screw Technique," Foot & Ankle International, vol. 41, No. 4, Apr. 1, 2020, published online: Dec. 26, 2019, pp. 426-436.
Talbot et al., "Assessing Sesamoid Subluxation: How Good is the AP Radiograph?," Foot and Ankle International, vol. 19, No. 8, Aug. 1998, pp. 547-554.
Wendl et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation of Scaphoid and Other Small Bone Fractures," Zimmer, 2003, 59 pages.
Weber et al., "A Simple System for Navigation of Bone Alignment Osteotomies of the Tibia," International Congress Series, vol. 1268, Jan. 2004, pp. 608-613, (Abstract Only).
Wukich et al., "Hypermobility of the First Tarsometatarsal Joint," Foot and Ankle Clinics, vol. 10, No. 1, Mar. 2005, pp. 157-166.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Toth et al., "The Effect of First Ray Shortening in the Development of Metatarsalgia in the Second Through Fourth Rays After Metatarsal Osteotomy," Foot & Ankle International, vol. 28, No. 1, Jan. 2007, pp. 61-63.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
"Visionaire: Patient Matched Cutting Blocks Surgical Procedure," Smith & Nephew, Inc., 2009, 2 pages.
Vitek, "Neue Techniken in der Fuchirurgie Das V-tek-System," ABW Wissenschaftsverlag GmbH, 2009, 11 pages, including English Abstract.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Wienke et al., "Bone Stimulation for Nonunions: What the Evidence Reveals," Podiatry Today, vol. 24, No. 9, Sep. 2011, pp. 52-57.
Tricot et al., "3D-corrective osteotomy using surgical guides for posttraumatic distal humeral deformity," Acta Orthopaedica Belgica, vol. 78, No. 4, 2012, pp. 538-542.
TempFix Spanning the Ankle Joint Half Pin and Transfixing Pin Techniques, Biomet Orthopedics, Surgical Technique, 2012, 16 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

(56) References Cited

OTHER PUBLICATIONS

Yasuda et al., "Proximal Supination Osteotomy of the First Metatarsal for Hallux Valgus," Foot and Ankle International, vol. 36, No. 6, Jun. 2015, pp. 696-704.
Defendant Fusion Orthopedics LLC's Invalidity Contentions, No. CV-22-00490-PHX-SRB, US District Court for the District of Arizona, Aug. 27, 2022, 41 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Stewart "Use for BME Speed Nitinol Staple Fixation for the Lapidus Procedure" date unknown, 1 page.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: a Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
D'Amico et al., "Motion of the First Ray: Clarification Through Investigation," Journal of the American Podiatry Association, vol. 69, No. 1, Jan. 1979, pp. 17-23.
Alvine et al., "Peg and Dowel Fusion of the Proximal Interphalangeal Joint," Foot & Ankle, vol. 1, No. 2, 1980, pp. 90-94.
Dayton et al., "Biwinged Excision for Round Pedal Lesions," The Journal of Foot and Ankle Surgery, vol. 35, No. 3, 1996, pp. 244-249.
Coughlin, "Fixation of the Lapidus Arthrodesis with a Plantar Interfragmentary Screw and Medial Low Profile Locking Plate," Orthopaedics and Traumatology, vol. 7, 1999, pp. 133-143.
Blomer, "Knieendoprothetik—Herstellerische Probleme und technologische Entwicklungen," Orthopade, vol. 29, 2000, pp. 688-696, including English Abstract on p. 689.
Bednarz et al., "Modified Lapidus Procedure for the Treatment of Hypermobile Hallux Valgus," Foot & Ankle International, vol. 21, No. 10, Oct. 2000, pp. 816-821.
Dayton et al., "Medial Incision Approach to the First Metatarsophalangeal Joint" The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Anderson et al., "Uncemented STAR Total Ankle Prostheses," The Journal of Bone and Joint Surgery, vol. 86(1, Suppl 2), Sep. 2004, pp. 103-111, (Abstract Only).
Coetzee et al., "The Lapidus Procedure: a Prospective Cohort Outcome Study," Foot & Ankle International, vol. 25, No. 8, Aug. 2004, pp. 526-531.
Dayton et al., "Early Weightbearing After First Metatarsophalangeal Joint Arthrodesis: a Retrospective Observational Case Analysis," The Journal of Foot and Ankle Surgery, vol. 43, No. 3, May/Jun. 2004, pp. 156-159.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Dayton et al., "Dorsal Suspension Stitch: an Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Bouaicha et al., "Fixation of Maximal Shift Scarf Osteotomy with Inside-Out Plating: Technique Tip," Foot & Ankle International, vol. 32, No. 5, May 2011, pp. 567-569.
Coetzee et al., "Revision Hallux Valgus Correction," Operative Techniques in Foot and Ankle Surgery, Section I, Chapter 15, 2011, pp. 84-96.
Dayton et al., "A User-Friendly Method of Pin Site Management for External Fixators," Foot and Ankle Specialist, Sep. 16, 2011, 4 pages.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Bauer et al., "Offset-V Osteotomy of the First Metatarsal Shaft in Hallux Abducto Valgus," McGlamrys Comprehensive Textbook of Foot and Ankle Surgery, Fourth Edition, vol. 1, Chapter 29, 2013, 26 pages.
Collan et al., "The biomechanics of the first metatarsal bone in hallux valgus: a preliminary study utilizing a weight bearing extremity CT," Foot and Ankle Surgery, vol. 19, 2013, pp. 155-161.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Effectiveness of a Locking Plate in Preserving Midcalcaneal Length and Positional Outcome after Evans Calcaneal Osteotomy: a Retrospective Pilot Study," The Journal of Foot and Ankle Surgery, vol. 52, 2013, pp. 710-713.
Dayton et al., "Principles of Management of Growth Plate Fractures in the Foot and Ankle," Clinics in Podiatric Medicine and Surgery, Pediatric Foot Deformities, Oct. 2013, 17 pages.
"Acumed Osteotomiesystem Operationstechnik," Acumed, 2014, 19 pages (including 3 pages English translation).
Catanese et al., "Measuring Sesamoid Position in Hallux Valgus: When Is the Sesamoid Axial View Necessary," Foot and Ankle Specialist, 2014, 3 pages.

(56) References Cited

OTHER PUBLICATIONS

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: a Case Series and Critical Review of the Literature," The Journal of Foot and Ankle Surgery, vol. 52, No. 3, May/Jun. 2013, pp. 348-354.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, Article in Press, 2014, 4 pages.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: a Case Series and Critical Review of the Literature," The Journal of Foot & Ankle Surgery, 2013, Article in Press, Mar. 1, 2013, 7 pages.
Dayton et al., "Reduction of the Intermetatarsal Angle after First Metatarsal Phalangeal Joint Arthrodesis: a Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Comparison of Complications for Internal and External Fixation for Charcot Reconstruction: a Systematic Review," The Journal of Foot and Ankle Surgery, Article in Press, 2015, 4 pages.
Dayton et al., "Complications of Metatarsal Suture Techniques for Bunion Correction: a Systematic Review of the Literature," The Journal of Foot and Ankle Surgery, Article in Press, 2015, 3 pages.
Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
"Accu-Cut Osteotomy Guide System," BioPro, Brochure, Oct. 2018, 2 pages.
DeCarbo et al., "The Weil Osteotomy: a Refresher," Techniques in Foot and Ankle Surgery, vol. 13, No. 4, Dec. 2014, pp. 191-198.
DeCarbo et al., "Resurfacing Interpositional Arthroplasty for Degenerative Joint Disease of the First Metatarsalphalangeal Joint," Podiatry Management, Jan. 2013, pp. 137-142.
Mizuno et al., "Detorsion Osteotomy of the First Metatarsal Bone in Hallux Valgus," Japanese Orthopaedic Association, Tokyo, 1956; 30:813-819.
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Sokoloff, "Lapidus Procedure," Textbook of Bunion Surgery, Chapter 15, 1981, pp. 277-287.
Odenbring et al., "A guide instrument for high tibial osteotomy," Acta Orthopaedica Scandinavica, vol. 60, No. 4, 1989, pp. 449-451.
Myerson, "Cuneiform-Metatarsal Arthrodesis," The Foot and Ankle, Chapter 9, 1997, pp. 107-117.
Patient to Patient Precision, Accu-Cut, Osteotomy Guide System, BioPro, Foot & Ankle International Journal, vol. 23, No. 8, Aug. 2002, 2 pages.
Schon et al., "Cuneiform-Metatarsal Arthrodesis for Hallux Valgus," The Foot and Ankle, Second Edition, Chapter 8, 2002, pp. 99-117.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Stahl et al., "Derotation of Post-Traumatic Femoral Deformities by Closed Intramedullary Sawing," Injury, vol. 37, No. 2, Feb. 2006, pp. 145-151, (Abstract Only).
Lee et al., "Technique Tip: Lateral Soft-Tissue Release for Correction of Hallux Valgus Through a Medial Incision Using a Dorsal Flap Over the First Metatarsal," Foot & Ankle International, vol. 28, No. 8, Aug. 2007, pp. 949-951.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).
Mote et al., "First Metatarsal-Cuneiform Arthrodesis for the Treatment of First Ray Pathology: a Technical Guide," JFAS Techniques Guide, vol. 48, No. 5, Sep./Oct. 2009, pp. 593-601.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Smith et al., "Opening Wedge Osteotomies for Correction of Hallux Valgus: a Review of Wedge Plate Fixation," Foot and Ankle Specialist, vol. 2, No. 6, Dec. 2009, pp. 277-282.
Magin, "Computernavigierter Gelenkersatz am Knie mit dem Orthopilot," Operative Orthopdie und Traumatologie, vol. 22, No. 1, 2010, pp. 63-80, including English Abstract on p. 64.
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
MiniRail System, Small Bone Innovations, Surgical Technique, 2010, 24 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

(56) References Cited

OTHER PUBLICATIONS

Stamatis et al., "Mini Locking Plate as Medial Buttress for Oblique Osteotomy for Hallux Valgus," Foot & Ankle International, vol. 31, No. 10, Oct. 2010, pp. 920-922.
Shurnas et al., "Proximal Metatarsal Opening Wedge Osteotomy," Operative Techniques in Foot and Ankle Surgery, Section I, Chapter 13, 2011, pp. 73-78.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.
"Speed Continuous Active Compression Implant," BioMedical Enterprises, Inc., A120-029 Rev. 3, 2013, 4 pages.
Modular Rail System: External Fixator, Smith & Nephew, Surgical Technique, 2013, 44 pages.
Otsuki et al., "Developing a novel custom cutting guide for curved per-acetabular osteotomy," International Orthopaedics (SICOT), vol. 37, 2013, pp. 1033-1038.
Peters et al., "Flexor Hallucis Longus Tendon Laceration as a Complication of Total Ankle Arthroplasty," Foot & Ankle International, vol. 34, No. 1, 2013, pp. 148-149.
Prophecy Inbone Preoperative Navigation Guides, Wright Medical Technology, Inc., Nov. 2013, 6 pages.
RAYHACK Ulnar Shortening Generation II Low-Profile Locking System Surgical Technique, Wright Medical Technology, Inc., Dec. 2013, 20 pages.
Sandhu et al., "Digital Arthrodesis With a One-Piece Memory Nitinol Intramedullary Fixation Device: a Retrospective Review," Foot and Ankle Specialist, vol. 6, No. 5, Oct. 2013, pp. 364-366.
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Lieske et al., "Implantation einer Sprunggelenktotalendo-prothese vom Typ Salto 2," Operative Orthopdie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.
Magin, "Die belastungsstabile Lapidus-Arthrodese bei Hallux-valgus-Deformitt mittels IVP-Plattenfixateur (V-TEK-System)," Operative Orthopdie und Traumatologie, vol. 26, No. 2, 2014, pp. 184-195, including English Abstract on p. 186.
Mini Joint Distractor, Arthrex, retrieved Dec. 19, 2014, from the Internet: <http://www.arthrex.com/foot-ankle/mini-joint-distractor/products>, 2 pages.
Nagy et al., "The AO Ulnar Shortening Osteotomy System Indications and Surgical Technique," Journal of Wrist Surgery, vol. 3, No. 2, 2014, pp. 91-97.
Osher et al., "Accurate Determination of Relative Metatarsal Protrusion with a Small Intermetatarsal Angle: a Novel Simplified Method," The Journal of Foot & Ankle Surgery, vol. 53, No. 5, Sep./Oct. 2014, published online: Jun. 3, 2014, pp. 548-556.
Rodriguez et al., "Ilizarov method of fixation for the management of pilon and distal tibial fractures in the compromised diabetic patient: a technique guide," The Foot and Ankle Journal Online, vol. 7, No. 2, 2014, 9 pages.
Rx-Fix Mini Rail External Fixator, Wright Medical Technology, Brochure, Aug. 15, 2014, 2 pages.
Small Bone External Fixation System, Acumed, Surgical Technique, Effective date Sep. 2014, 8 pages.
Smith & Nephew scores a HAT-TRICK with its entry into the high-growth hammer toe repair market, Smith & Nephew, Jul. 31, 2014, 2 pages.
"Reconstructive Surgery of the Foot & Ankle," The Podiatry Institute, Update 2015, Conference Program, May 2015, 28 pages.
Stableloc External Fixation System, Acumed, Product Overview, Effective date Sep. 2015, 4 pages.
Michelangelo Bunion System, Surgical Technique, Instratek Incorporated, publication date unknown, 4 pages.
Caldarella, "Lapidus Arthrodesis: Patient Selection and Surgical Technique", Chapter 24, The Podiatry Institute, 1998, pp. 142-149.
Chambers, "The Frontal Plane Derotational Head Osteotomy for Correction of Valgus Rotation of the Hallux" , Chapter 52, The Podiatry Institute, 2004, pp. 301-307.
Cottom et al., "Fixation of Lapidus Arthrodesis with a Plantar Interfragmentary Screw and Medial Locking Plate: A Report of 88 Cases", The Journal of Foot & Ankle Surgery 52, 2013, pp. 465-469.
Innomed, Inc., "Medial Malleolar / Bone Fragment Clamp" , Brochure, 2002, p. 1.
Lapidus, "Operative Correction of the Metatarsus Varus Primus in Hallux Valgus" , Sugery, Gynecology and Obstetrics, The Surgical Publishing Company of Chicago, Jan. 1934, p. 10.
McGlamry, "Lapidus XL: Gaining Stability Without Compromising Length", Chapter 17, The Podiatry Institute, 2003, pp. 74-77.
Olms, "The Modified Lapidus Arthrodesis for the Correction of the Hallux Valgus Deformity: Retrospective Analysis of 182 Cases", Chapter 49, The Podiatry Institute, 2004, pp. 285-288.
Orthomed, Inc., "OrthoMed Bone Holding Instruments Product Catalog" , Section L, Available for download Nov. 2, 2013, p. 21.
Schuberth et al., "Minimally Invasive Lapidus Procedure", Chapter 34, The Podiatry Institute, 2000, pp. 203-207.
Malay et al., "Instrumentation", Chapter 1, McGlamry's Comprehensive Textbook of Foot and Ankle Surgery, Fourth Edition, Published Wolters Kluwer Health Lippincott Williams & Wilkins, 2013, pp. 3-14.
Synthes, Inc., "Collinear Reduction Clamp—Handling Technique", Synthes, Sep. 2008, p. 16.
Testa et al. "The Sesamoid Apparatus Position in Hallux Valgus Surgery", Chapter 1, The Podiatry Institute, 2005, pp. 1-7.
Yu et al., "Hallux Valgus Surgery and the Sesamoid Apparatus" , Chapter 9, The Podiatry Institute, 1997, pp. 42-49.
Labib, "Lapidus Procedure for Hallux Valgus Correction with Mini TightRope", Arthrex, Published Apr. 15, 2013, Retrieved from: https://www.arthrex.com/resources/VID1-0433-EN/lapidus-procedure-for-hallux-valgus-correction-with-mini-tightrope?referringteam=foot_and_ankle, Video captured Jul. 10, 2025, p. 4.
Defendant Stryker Corporation and Wright Medical Technology, Inc., Invalidity Contentions, No. 2:24-cv-09763-JKS-MAH, US District Court for the District of New Jersey, Aug. 4, 2025, 193 pages.
Downey et al., "Congenital Overlapping Fifth Toe Deformity", Chapter 17, McGlamry's Comprehensive Textbook of Foot and Ankle Surgery, Fourth Edition, Published Wolters Kluwer Health Lippincott Williams & Wilkins, 2013, pp. 154-164.
Dunn et al., "Tailor's Bunion Deformity", Chapter 23, McGlamry's Comprehensive Textbook of Foot and Ankle Surgery, Fourth Edition, Published Wolters Kluwer Health Lippincott Williams & Wilkins, 2013, pp. 235-242.
DiDomenico et al., "Lapidus Bunionectomy", Chapter 31, McGlamry's Comprehensive Textbook of Foot and Ankle Surgery, Fourth Edition, Published Wolters Kluwer Health Lippincott Williams & Wilkins, 2013, pp. 322-330.
Vanore et al., "First Metatarsophalangeal Joint Arthroplasty", Chapter 34, McGlamry's Comprehensive Textbook of Foot and Ankle Surgery, Fourth Edition, Published Wolters Kluwer Health Lippincott Williams & Wilkins, 2013, pp. 362-399.
Claim Charts for Fishco Article, "Making the Lapidus Easy" The Podiatry Institute, Apr. 2014, Exhibit 1 of Defendant Stryker Corporation and Wright Medical Technology, Inc., Invalidity Contentions, No. 2:24-CV-09763-JKS-MAH, US District Court for the District of New Jersey, Aug. 4, 2025, 497 pages.
Claim Charts for McGlamry's Book, "McGlamry's Comprehensive Textbook of Foot and Ankle Surgery", 4th ed., vol. 1, Published 2013, Exhibit 2 of Defendant Stryker Corporation and Wright

(56) References Cited

OTHER PUBLICATIONS

Medical Technology, Inc., Invalidity Contentions, No. 2:24-CV-09763-JKS-MAH, US District Court for the District of New Jersey, Aug. 4, 2025, 535 pages.
Claim Charts for Cottom Article, " Fixation of Lapidus Arthrodesis with a Plantar Interfragmentary Screw and Medial Locking Plate: A Report of 88 Cases" The Journal of Foot & Ankle Surgery, vol. 52, pp. 465-469, Exhibit 3 of Defendant Stryker Corporation and Wright Medical Technology, Inc., Invalidity Contentions, No. 2:24-CV-09763-JKS-MAH, US District Court for the District of New Jersey, Aug. 4, 2025, 639 pages.
Claim Charts for Arthrex Labib Video, " Lapidus Procedure for Hallux Valgus Correction with Mini TightRope", Arthrex. com, was published on Apr. 15, 2013, Exhibit 4 of Defendant Stryker Corporation and Wright Medical Technology, Inc., Invalidity Contentions, No. 2:24-CV-09763-JKS-MAH, US District Court for the District of New Jersey, Aug. 4, 2025, 579 pages.
Claim Charts for U.S. Pat. No. 8,313,492 ("Wong"), "Drill Guide Assembly", Provisional Application Filed May 29, 2009, Issued Nov. 20, 2012, Exhibit 5 of Defendant Stryker Corporation and Wright Medical Technology, Inc., Invalidity Contentions, No. 2:24-CV-09763-JKS-MAH, US District Court for the District of New Jersey, Aug. 4, 2025, 964 pages.
Claim Chart for U.S. Publication No. 2016/0213384 ("Fallin"), "Freeform Tri-Planar Osteotomy Guide and Method", Provisional Application Filed Dec. 4, 2015, Exhibit 6 of Defendant Stryker Corporation and Wright Medical Technology, Inc., Invalidity Contentions, No. 2:24-CV-09763-JKS-MAH, US District Court for the District of New Jersey, Aug. 4, 2025, 168 pages.
Claim Chart for McGlamry's Book, " McGlamry's Comprehensive Textbook of Foot and Ankle Surgery", 4th ed., vol. 1, Published 2013, Exhibit 7 of Defendant Stryker Corporation and Wright Medical Technology, Inc., Invalidity Contentions, No. 2:24-CV-09763-JKS-MAH, US District Court for the District of New Jersey, Aug. 4, 2025, 234 pages.
Claim Chart for Fishco Article, "Making the Lapidus Easy," The Podiatry Institute, Apr. 2014, Exhibit 8 of Defendant Stryker Corporation and Wright Medical Technology, Inc., Invalidity Contentions, No. 2:24-CV-09763-JKS-MAH, US District Court for the District of New Jersey, Aug. 4, 2025, 250 pages.
Claim Chart for Arthrex Labib Video, " Lapidus Procedure for Hallux Valgus Correction with Mini TightRope", Arthrex. com, was published on Apr. 15, 2013, Exhibit 9 of Defendant Stryker Corporation and Wright Medical Technology, Inc., Invalidity Contentions, No. 2:24-CV-09763-JKS-MAH, US District Court for the District of New Jersey, Aug. 4, 2025, 215 pages.
Baravarian et al., "Lapidus Bunionectomy: arthrodesis of the first metatarsocunieform joint" , Clin Podiatr Surg, 21, 2004, pp. 97-111.
Dunn et al., "Principles of Arthrodesis", Chapter 55, McGlamrys Comprehensive Textbook of Foot and Ankle Surgery, Fourth Edition, Published Wolters Kluwer Health Lippincott Williams & Wilkins, 2013, pp. 803-809.
Hofbauer et al., "The Lapidus Procedure", Clinics in Podiatric Medicine and Surgery, vol. 13, No. 3, Jul. 1996, pp. 485-496.
Judge, "Complications in Hallux Abducto Valgus Surgery (Excluding Hallux Varus)" , Chapter 36, McGlamrys Comprehensive Textbook of Foot and Ankle Surgery, Fourth Edition, Published Wolters Kluwer Health Lippincott Williams & Wilkins, 2013, pp. 417-460.
Mothershed, "Principles of Arthrodesis", Chapter 16, Part 1 & 2, McGlamrys Comprehensive Textbook of Foot and Ankle Surgery, Third Edition, Published Wolters Kluwer Health Lippincott Williams & Wilkins, 2004, pp. 529-556.
Okuda et al., "Proximal abduction-supination osteotomy of the first metatarsal for adolescent hallux valgus: a preliminary report" , J Orthop Sci, 18, Published Mar. 20, 2013, pp. 419-425.
Franssen et al., "One Century of Kirschner wires and Kirschner wire insertion techniques: A historical review", Acta Orthopaedica Belgica, vol. 76, pp. 1-6.
Paragon 28, "Surgical Technique Guide Bun-Yo-Matic Lapidus Clamp System" , Apr. 25, 2025, p. 32.
Schmid et al., "The Modified Lapidus Fusion" , Foot Ankle Clin N Am, 19, 2014, pp. 223-233.
Toolan, "Surgical Strategies: The Lapidus Procedure" , Foot & Ankle International, vol. 28, No. 10, Oct. 2007, pp. 1108-1114.
Young et al., "New Techniques and Alternative Fixation for the Lapidus Arthrodesis", Clin Podiatr Med Surg, 30, 2013, pp. 423-434.
Paragon 28, Inc., "Petition for Inter Partes Review of U.S. Pat. No. 12, 102,368", *Paragon 28, Inc. Petitioner* v. *Treace Medical Concepts Inc.* Patent Owner, Case IPR2026-00194, Filed Jan. 5, 2026, p. 114.
"Declaration of Dr. Steven K. Neufeld, MD, in Support of Petition for Inter Partes Review of U.S. Pat. No. 12,102,368", *Paragon 28, Inc. Petitioner* v. *Treace Medical Concepts Inc.* Patent Owner, Case IPR2026-00194, Executed Dec. 31, 2025, p. 142.
Paragon 28, Inc., "Petition for Post-Grant Review of U.S. Pat. No. 12,268, 397", *Paragon 28, Inc. Petitioner* v. *Treace Medical Concepts Inc.* Patent Owner, Case PGR2026-00017, Filed Dec. 19, 2025, p. 126.
"Declaration of Dr. Steven K. Neufeld, MD, in Support of Petition for Post-Grant Review of U.S. Pat. No. 12,268,397", *Paragon 28, Inc. Petitioner* v. *Treace Medical Concepts Inc.* Patent Owner, Case PGR2026-00017, Executed Dec. 18, 2025, p. 104.
Paragon 28, Inc., "Petition for Post Grant Review of U.S. Pat. No. 12,268,428", *Paragon 28, Inc. Petitioner* v. *Treace Medical Concepts Inc.* Patent Owner, Case PGR2026-00020, Filed Dec. 23, 2025, p. 148.
"Declaration of Dr. Steven K. Neufeld, MD, in Support of Petition for Post-Grant Review of U.S. Pat. No. 12,268,428", *Paragon 28, INC.* Petitioner v. *Treace Medical Concepts Inc.* Patent Owner, Case PGR2026-00020, Executed Dec. 23, 2025, p. 155.
Paragon 28, Inc., "Petition for Post-Grant Review of U.S. Pat. No. 12,274,481", *Paragon 28, Inc.* Petitioner v. *Treace Medical Concepts Inc.* Patent Owner, Case PGR2026-00022, Filed Jan. 13, 2026, p. 138.
"Declaration of Dr. Steven K. Neufeld, MD, in Support of Petition for Post-Grant Review of U.S. Pat. No. 12,274,481", *Paragon 28, Inc.* Petitioner v. *Treace Medical Concepts Inc.* Patent Owner, Case PGR2026-00022, Executed Jan. 13, 2026, p. 179.
Paragon 28, Inc., "Petition for Post-Grant Review of U.S. Pat. No. 12,349,941", *Paragon 28, Inc.* Petitioner v. *Treace Medical Concepts Inc.* Patent Owner, Case PGR2026-00031, Filed Mar. 3, 2026, p. 137.
"Declaration of Dr. Steven K. Neufeld, MD, in Support of Petition for Post-Grant Review of U.S. Pat. No. 12,349,941", *Paragon 28, Inc.* Petitioner v. *Treace Medical Concepts Inc.* Patent Owner, Case PGR2026-00031, Executed Mar. 3, 2026, p. 172.
Treace Medical Concepts, Inc., "Patent Owner's Preliminary Response", *Paragon 28, Inc.* Petitioner v. *Treace Medical Concepts Inc.* Patent Owner, Case PGR2026-00017, U.S. Pat. No. 12,268,397, Filed Apr. 1, 2026, p. 69.
Treace Medical Concepts, Inc., "Patent Owner's Preliminary Response", *Paragon 28, Inc.* Petitioner v. *Treace Medical Concepts Inc.* Patent Owner, Case PGR2026-00020, U.S. Pat. No. 12,268,428, Filed Apr. 6, 2026, p. 33.
Treace Medical Concepts, Inc., "Patent Owner's Preliminary Response", *Paragon 28, Inc.* Petitioner v. *Treace Medical Concepts Inc.* Patent Owner, Case PGR2026-00194, U.S. Pat. No. 12,102,368, Filed Apr. 13, 2026, p. 51.
Treace Medical Concepts, Inc., "Patent Owner's Preliminary Response", *Paragon 28, Inc.* Petitioner v. *Treace Medical Concepts Inc.* Patent Owner, Case PGR2026-00022, U.S. Pat. No. 12,274,481, Filed Apr. 22, 2026, p. 42.
"Declaration of Michelle L. Warmath and English Translation of European Patent Application EP 1508316 A1", dated Nov. 22, 2025, p. 59.
"Declaration of Daniel C. Farber, MD, in Support of the Patent Owner's Preliminary Response", *Paragon 28, Inc.* Petitioner v. *Treace Medical Concepts Inc.* Patent Owner, Case PGR2026-00017, U.S. Pat. No. 12,268,397, Executed Mar. 31, 2026, p. 18.
"Declaration of Daniel C. Farber, MD, in Support of the Patent Owner's Preliminary Response", *Paragon 28, Inc.* Petitioner v.

(56) References Cited

OTHER PUBLICATIONS

*Treace Medical Concepts Inc.* Patent Owner, Case PGR2026-00020, U.S. Pat. No. 12,268,428, Executed Mar. 31, 2026, p. 8.
"Declaration of Daniel C. Farber, MD, in Support of the Patent Owner's Preliminary Response", Paragon 28, INC. Petitioner v. Treace Medical Concepts Inc. Patent Owner, Case PGR2026-00194, U.S. Pat. No. 12, 102,368, Executed Apr. 10, 2026, p. 18.
"Declaration of Daniel C. Farber, Md, in Support of the Patent Owner's Preliminary Response", Paragon 28, INC. Petitioner v. Treace Medical Concepts Inc. Patent Owner, Case PGR2026-00022, U.S. Pat. No. 12,274,481, Executed Apr. 15, 2026, p. 15.

* cited by examiner

Rotate the metatarsal in the frontal plane along the bone axis to make the distal (black pins) vertical. Proximal pins are cross hatched.

THEN

Axial plane angle correction (looking from top-down on foot).

300
302
310
320
330
340
350
360
370

PIVOTABLE BONE CUTTING GUIDE USEFUL FOR BONE REALIGNMENT AND COMPRESSION TECHNIQUES

RELATED APPLICATION

This application is a continuation of U.S. patent application Ser. No. 17/106,314, filed Nov. 30, 2020, which is a divisional of U.S. patent application Ser. No. 15/047,288, filed Feb. 18, 2016 and issued as U.S. Pat. No. 10,849,631 on Feb. 18, 2016, which claims the benefit of U.S. Provisional Application Ser. No. 62/117,747, filed Feb. 18, 2015. The entire contents of each of these applications are incorporated herein by reference.

TECHNICAL FIELD

This disclosure relates generally to devices and methods for positioning and cutting bones.

BACKGROUND

Bones, such as the bones of a foot or ankle, may be anatomically misaligned. In certain circumstances, surgical intervention is required to correctly align the bones to reduce patient discomfort and improve patient quality of life.

SUMMARY

In general, this disclosure is directed to bone cutting guide systems and techniques for realigning and compressing bone together, such as bones cut using the cutting guide system. In some examples, a bone cutting guide has as a main block that has one or more guide members pivotably attached to the main block. The one or more guide members each define a guide surface, such as a planar surface, along which a cutting instrument can be placed in abutment and translated. In use, the main block can be positioned at a desired anatomical location, such as spanning a joint between two bones (e.g., a tarsal-metatarsal joint). Each guide member can be pivotably articulated relative to the main block to precisely position the cut guide surface provided by the guide member for performing a cutting operation. For instance, in one specific application where the cutting guide is configured with two guide members, one guide member can be positioned to cut an end of a first metatarsal while the second guide member is positioned to cut an opposing end of a medial cuneiform. Depending on the configuration of the cut guide, the one or more guide members may also be elevationally adjusted relative to the main block to position the guide members at different elevations (e.g., heights) on the bones being operated upon.

After suitably positioning the one or more guide members relative to the main block and/or the bones being operated upon, the guide members may be provisionally fixated to prevent further movement of the guide members during cutting. For example, each guide member may include one or more fixation apertures configured to receive a fixation member, such as a pin, wire, or screw. The clinician can insert a fixation member through the fixation aperture of the guide member and into the underlying bone, thereby fixating the guide member to the bone. In some configurations, the main block is detachable from the one or more guide members such that, after positioning and fixating the guide members, the block is removed from the guide members to provide better access to the guide surfaces defined by the guide members. In either case, the clinician can use the guide surface defined by each guide member to guide a cutting instrument. For example, the clinician can place the cutting instrument in contact with the guide surface and translate the cutting instrument along the guide surface into the underlying bone, thereby using the guide surface to guide the cutting operation. After making one or more cuts using the guide members, the guide members can be removed from the bone(s) to which the guide members are provisionally fixated.

In addition to or in lieu of utilizing the cutting guide with pivotable guide members, a clinician may compress different bone portions together using a bone fixation pin during a bone correction procedure. For example, the clinician may utilize a bone fixation pin that has a threaded leading end and a collar positioned along the length of the shaft. The collar may be a region of the shaft that has a larger cross-sectional dimension (e.g., diameter) than at least the portion of the shaft distal of the collar. In use, the clinician can drive the leading end of the shaft into and through a first bone portion and into a second bone portion until the collar contacts the first bone portion. The clinician may further drive the shaft toward the second bone portion, causing the collar to press upon the first bone portion and move the first bone portion toward the second bone portion, thereby compressing the bone portions together. The clinician may fixate the bone portions together after compressing the bone portions. For example, the clinician may attach one or more bone plates to the bone portions to hold the bone portions together. Additionally or alternatively, in applications where the bone fixation pin is detachable proximally of the collar, the clinician may detach the bone pin proximally of the collar to leave an implant portion of the pin within the bones.

As one example application, a clinician may perform a tarsal-metatarsal joint fusion procedure by preparing an end of a first metatarsal and an end of a medial cuneiform opposing the end of the first metatarsal. The clinician may use a cut guide having one or more pivotably connected guide members to prepare the ends of the bones using a cutting instrument. Alternatively, the clinician may prepare the end of one or both bones using a cut guide having a different configuration or may prepare the bones free hand (e.g., by cutting without a guide and/or morselizing without a guide). In either case, the clinician can move the first metatarsal relative to a second metatarsal, either before or after preparing the ends of the bones, for example by adjusting the first metatarsal from an anatomically misaligned position with respect to the second metatarsal to a position that is anatomically aligned with respect to the second metatarsal. In some examples, the clinician drives the bone fixation pin into the metatarsal and uses the bone fixation pin as a lever to manipulate the position of the first metatarsal relative to the second metatarsal.

After optionally aligning the first metatarsal, the clinician can drive the bone fixation pin through one side of the first metatarsal, out a generally opposite side of the first metatarsal, and into the medial cuneiform. Alternatively, the clinician may drive the bone fixation pin through the medial cuneiform, out a generally opposite side of the medial cuneiform, and into the first metatarsal. In either application, the clinician can continue driving the bone fixation pin forward, the first metatarsal and medial cuneiform to compress together (e.g., by closing the tarsal-metatarsal joint gap). The clinician can then fixate the first metatarsal and medial cuneiform together, e.g., to hold the first metatarsal in an anatomically aligned position with respect to the second metatarsal.

In one example, a method of compressing adjacent bone portions together is described. The method includes providing a bone fixation pin having a length, a threaded end portion, and a collar, driving the threaded end portion into a first bone portion, and driving the threaded end portion through the first bone portion. The method further involves driving the threaded end portion into a second bone portion until the collar is in apposition to the first bone portion and further driving the threaded end portion into the second bone portion to compress together the first bone portion and the second bone portion.

In another example, a bone cutting guide is described that includes a block and a first guide member. The first guide member is pivotally attached to the block and includes a first guide surface defining a first plane.

In another example, a method of cutting bones is described. The method includes positioning a projection of a block at least partially within a space defined between bones, where the block is pivotally connected to a first guide member. The method further involves aligning the first guide member at a location to be cut, where a first guide surface of the first guide member is positioned at the location to be cut. In addition, the method includes fixing the first guide member to a bone and making a first cut at the location to be cut by placing a cutting member in apposition to the first guide surface.

In another example, a method of aligning bone is described that includes inserting a first fixation pin in a first bone portion at a first angle and inserting a second fixation pin in a second bone portion at a second angle, where the first and second angles being different. The method further involves positioning the first and second bone portions with respect to each other by manipulating the first fixation pin and the second fixation pin.

The details of one or more examples are set forth in the accompanying drawings and the description below. Other features, objects, and advantages will be apparent from the description and drawings, and from the claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and dimensions are provided for selected elements, and all other elements employ that which is known to those of ordinary skill in the field of the invention. Those skilled in the art will recognize that many of the noted examples have a variety of suitable alternatives.

Embodiments of the present invention include a bone cutting guide. In an exemplary application, the bone cutting guide can be useful during a surgical procedure, such as a bone alignment, osteotomy, fusion procedure, and/or other procedures where one or more bones are to be cut. Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing the bone cutting guide can be performed to correct an alignment between a metatarsal (e.g. a first metatarsal) and a cuneiform (e.g., a first cuneiform), such as a bunion correction. An example of such a procedure is a lapidus procedure (also known as a first tarsal-metatarsal fusion). In another example, the procedure can be performed by modifying an alignment of a metatarsal (e.g. a first metatarsal). An example of such a procedure is a basilar metatarsal osteotomy procedure. As yet another example, the procedure can be a first metatarsal-phalangeal joint (MTP) procedure. In some embodiments, the guide is disposable, such that it is discarded after the surgical procedure.

Figure 1:
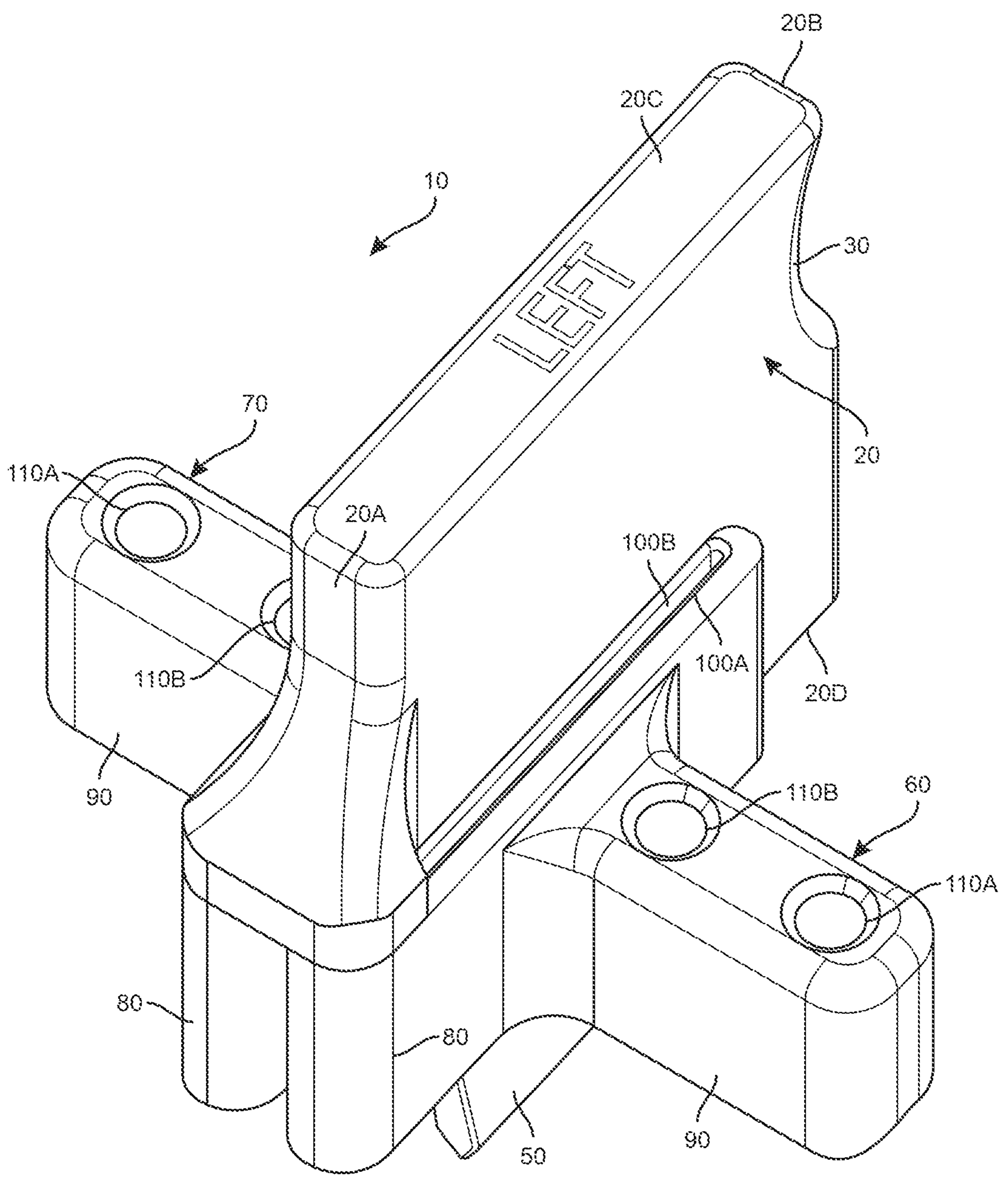
FIG. 1 is a perspective view of an embodiment of a bone cutting guide.
Figure 2:
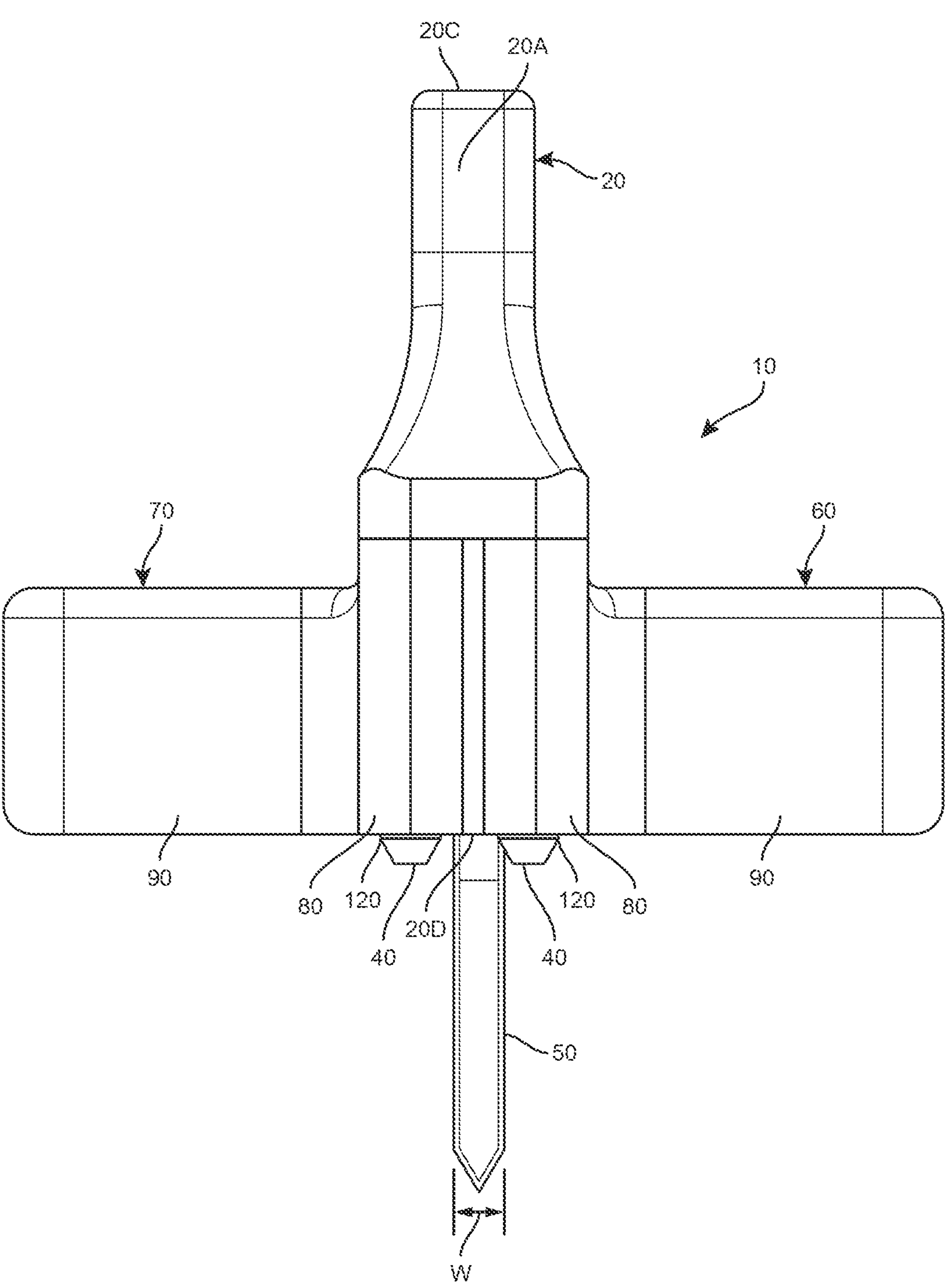
FIG. 2 is a side elevational view of the bone cutting guide of FIG. 1.

FIGS. 1 and 2 show an embodiment of a bone cutting guide 10. FIG. 1 is a perspective view of the bone cutting guide 10, while FIG. 2 is a side elevational view of the bone cutting guide 10. As shown, the bone cutting guide 10 can include a block 20 having first and second side ends 20A and 20B as well as a top end 20C and a bottom end 20D. The block 20 can be made from a biocompatible material, such as a biocompatible metal or polymeric material. In the illustrated embodiment, the block 20 is shaped and dimensioned such that the block 20 is capable of being gripped by hand during a surgical procedure. For example, the block 20 may include a recess 30 on one or more ends, such as the end 20B as shown, to assist in gripping the block 20. However, in other embodiments the block 20 can have various shapes and dimensions.

As shown in FIG. 2, the block 20 can have one or more guide attachment members 40. For the bone cutting guide 10 as shown, the one or more guide attachment members 40 are pivotably attached on the end 20A of the block 20 and rotatable about an axis extending through end 20A. In one embodiment, the one or more guide attachment members 40 can be fixed to the block 20 on an end of the members 40 nearest the top end 20C and free on an end of the attachment members 40 nearest the bottom end 20D. In such a configuration, the one or more members 40 can extend or project out from the end fixed to the block 20 in a direction that is generally parallel to an axis of the block 20 extending from the top end 20C to the bottom end 20D. In other configurations of the block 20 that include the guide attachment members 40, the members 40 can be fixed at various positions on the block 20 and extend out from the block 20 at any angle. In the embodiment shown, the members 40 define a generally cylindrical shape.

The block 20 can additionally include a projection 50 that extends out from an end, such as the bottom end 20D as illustrated, of the block 20. In an exemplary application, the bottom end 20D of the block 20 can be positioned so as to interface with, for instance, two bones while the projection 50 is configured to extend into a space defined between the bones (e.g. a joint between two bones, or a space between two bone portions of a fractured bone), thereby helping to anatomically align the guide with respect to the space. As such, depending on the application of the bone cutting guide 10, the projection 50 may have a width W that is dimensioned so as to be able to fit into the space defined between bones as desired. As shown, the projection 50 may be a planar member having two surfaces separated by a distance. In the embodiment shown, the distance, W, in generally constant, and a leading edge of the projection 50 is provided with a wedge or taper to facilitate insertion into a space. In other embodiments, the distance (e.g., thickness and/or width) may vary from a narrower dimension near the leading region to a wider dimension near a proximal region.

The bone cutting guide 10 can also include one or more guide members positionable with respect to block 20 which, in the illustrated example, are shown as a first guide member 60 and a second guide member 70. The guide members 60 and 70 may be made of metal or any other suitable material. The guide members 60 and 70 can each have a flange 80 and a support 90. The flange 80 is connected to the support 90, and in some embodiments the flange 80 and the support 90 can be one integral component. As will be discussed, the flange 80 may mate with a pin projecting from block 20 to form a hinge about which the flange and/or support 90 can rotate.

Each flange 80 may include a first guide surface 100A configured to guide a cutting instrument, such as a saw blade, in a desired plane. In some embodiments, one or both flanges include a second guide surface 100B. The first and second guide surfaces 100A and 100B can be adjacent surfaces facing one another with a space (e.g., opening or gap) defined in the flange 80 between the first and second guide surfaces 100A and 100B. The space may be configured (e.g., sized and/or shaped) for receiving a cutting instrument, such as a saw blade. The surfaces 100A and 100B can be configured for holding the cutting instrument in a desired plane during a cutting operation. For example, in use, a clinician may position a cutting instrument (e.g., saw blade, rotary burr, osteotome) against first guide surface 100A, against second guide surface 100B, and/or in the space between the first and second guide surfaces. The clinician may then translate the cutting instrument along and/or between the guide surfaces, thereby using the guide surfaces to guide a cut made on bone.

In general, the lateral distance between a surface of the block 20 and the first guide surface 100A will define an amount of bone to be cut. In some configurations, the distance is adjustable to adjust the amount (e.g., width) of bone cut. In some embodiments, this distance is between about one to about two and a half millimeters. In some embodiments, a height of the first guide surface 100A is set to correspond to a known cutting instrument length when the guide is positioned on bone, such that cuts of known depths can be made relying on the guide surface.

As shown, the first guide surface 100A can be a surface of the flange 80 extending from an edge of the flange 80 that connects to the support 90. The second guide surface 100B can be a surface of the flange 80 extending from an edge of the flange 80 that interfaces with the block 20. In the illustrated embodiment, the guide surfaces 100A and 100B are both single, continuous surfaces lacking any openings on their face. In some embodiments (not illustrated), a guide surface, for instance the second guide surface 100B, can contain a gap or opening such that the guide surface is not a single, continuous surface.

In general, the first guide surface 100A defines a first plane and the second guide surface 100B defines a second plane. As shown, the first guide surface 100A and the second guide surface 100B can be configured such that the first plane is parallel to the second plane, with a space (defined in the flange 80) between the first and second guide surfaces. In further embodiments (not illustrated), the guide surfaces 100A and 100B can be configured such that the first and/or second planes are skewed. Although the guide surfaces 100A and 100B are shown to be on the flange 80, in other embodiments, the guide members 60 and/or 70 may have the guide surfaces 100A and 100B (and thus the space defined between the guide surfaces 100A and 100B) at other locations. For example, the guide surfaces 100A and 100B may be included as part of the support 90, such that the space defined in the flange 80 between the guide surfaces 100A and 100B would instead be defined in the support 90.

The support 90 of each guide member 60 and 70 can be used to align the cut guide with an anatomic axis (e.g., long axis, anterior-posterior axis) of a bone or a foot. In the embodiment shown, support 90 is generally linear, although in other embodiments, support 90 may include a curve in on or more planes. In some embodiments, not shown, the support 90 is adjustable relative to flange 80 to improve its anatomic fit when bone cutting guide 10 is installed on a patient. For example, an end of the support 90 can be provided with an adjustment screw to elevationally adjust the support with respect to the bone on which cut guide 10 is positioned.

The support 90 of each guide member 60 and 70 can include one or more fixation apertures 110A and/or 110B. The fixation apertures 110A and 110B may extend through the support 90. Each of the fixation apertures 110A and 110B can receive, for example, a preparation fixation pin that extends through the support 90 at the fixation apertures 110A and 110B such that an end of the preparation fixation pin can be fixed to a bone. In the illustrated embodiment of FIG. 1, the fixation apertures 110A and 110B are generally vertical and are located on opposite ends of the support 90. Specifically, in the embodiment shown, the fixation apertures 110A and 110B as shown are located on opposite ends of a longitudinal axis of the support 90 that extends perpendicular to the flange 80, and thus the first and second guide surfaces 100A and 100B. However, in other embodiments, the support 90 can extend at various angles from the flange 80 and the one or more fixation apertures 110A and 110B can be positioned at various locations on the guide members 60 and 70 (e.g. the flange 80). Further, either or both supports 90 can include any desired number of fixation apertures (e.g., 1, 2, 3, or 4) aligned at any desired orientation.

Figure 3A:
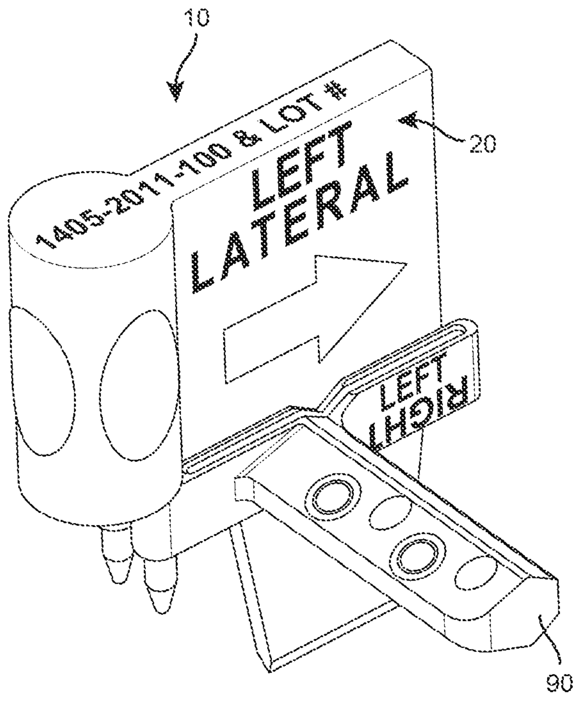
FIGS. 3A and 3B are perspective views of another embodiment of a bone cutting guide showing example fixation aperture arrangements that can be used on the bone cutting guide of FIG. 1.
Figure 3B:
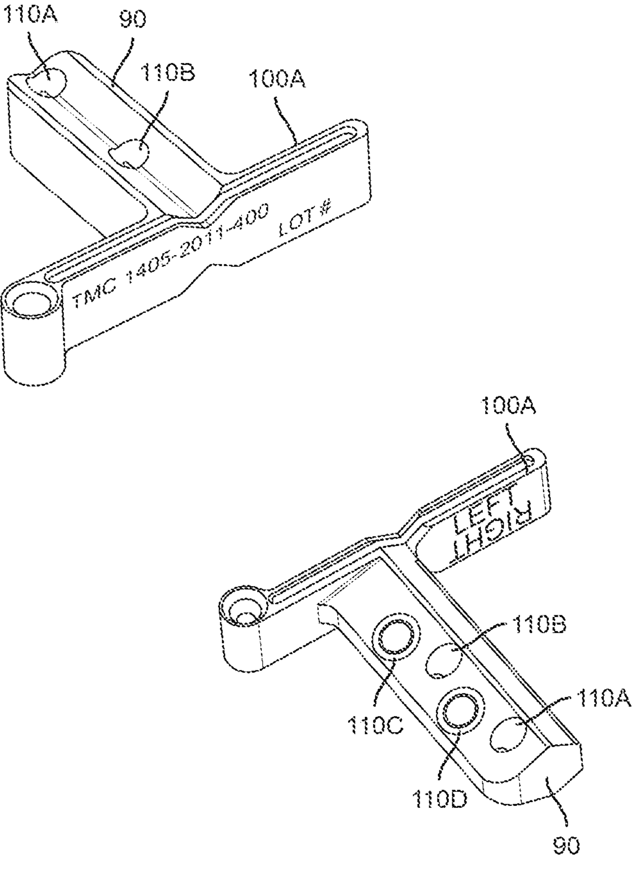

The one or more fixation apertures provided on each of first guide member 60 and second guide member 70 can have a variety of different configurations. FIGS. 3A and 3B are perspective views of another embodiment of bone cutting guide 10 showing example fixation aperture arrangements. FIG. 3B shows the bone cutting guide of FIG. 3A with block 20 disconnected for purposes of illustration. As shown, at least one fixation aperture 110A, 110B is provided at a skewed angle relative to a vertical axis of the support 90, the first surface 100A, a vertical axis of the block 20, and/or at least one other fixation aperture. In some embodiments, the skewed angle is between about 5 degrees and about 45 degrees from vertical. In certain embodiments, the skewed angle is between about 10 degrees and about 30 degrees. In a specific embodiment, the skewed angle is about 20 degrees. The skewed angle can be useful for guiding a preparation fixation pin into bone at a known angle other than vertical. In the embodiment shown in FIG. 1B, one of the supports 90 has vertical fixation apertures 110A and 110B, and the other of the supports has vertical fixation apertures 110A and 110B and skewed fixation apertures 110C and 110D.

With further reference to FIGS. 1 and 2, first guide member 60 and/or second guide member 70 may be pivotally attached to the block 20 such that the guide member 60 and/or 70 can pivot with respect to the block 20. For example, in one embodiment, to pivotally attach the guide member 60 and/or 70 to the block 20, the guide member 60 and/or 70 may include an aperture 120 that receives the guide attachment member 40 of the block 20. The aperture may define a cylindrical shape sized to mate with the attachment member 40. In the illustrated embodiment, the aperture 120 is included on an end of the flange 80 adjacent the first and second guide surfaces 100A and 100B. In other variations, the aperture 120 can be positioned at other locations on the guide member 60 and/or 70. Further, in some embodiments (not shown), the block 20 can include the aperture 120 and the guide member 60 and/or 70 can include the attachment member 40.

In either configuration, the aperture 120 can be aligned with the guide attachment member 40, and the guide member 60 and/or 70 can be attached to the block 20 by mating the attachment member 40 and the aperture 120. In some embodiments, the pivotable connection established between guide members 60 and/or 70 and block 20 is further adjustable to adjust the elevation of the guide members relative to the block. For example, the guide member 60 and/or 70 may attach to block 20 by sliding upwardly along the attachment member 40 until the guide member 60 and/or 70 contacts a bottom surface of the block 20. The guide member 60 and/or 70 can be free (e.g., open) at an end opposite from the end contacting the block 20, which can allow the guide member 60 and/or 70 to translate along the guide attachment member 40 such that the guide members 60 and 70 may be at different elevations with respect to the block 20. In some embodiments, the block 20 can be detached from the guide members 60 and/or 70 while the guide members are held on bone by preparation fixation pins. In such embodiments, a retention mechanism may be provided to facilitate retaining the guide members to the block during handling and prior to installation of the guide on bone. For example, the retention mechanism may include a magnet disposed within the block, a mechanical feature, and/or a surface treatment, such as a coating or roughening, to increase friction between the guide members and the attachment members.

In some examples, the guide member 60 and/or 70 is attached to the block 20 in a way that allows the guide member 60 and/or 70 to independently pivot with respect to the block 20 and to independently translate with respect to the block 20. The guide member 60 and/or 70 can be pivotally attached to the block 20 in numerous ways and at various locations on the block 20. For instance, as illustrated, the guide members 60 and 70 are pivotally attached to the block 20 on the same end 20A of the block 20 and radially spaced from each other on that end 20A. In this configuration, the guide members 60 and 70 pivot about the block 20 at an end 20A opposite an end 20B of the block 20. Additionally, the embodiment shown has the guide members 60 and 70 configured to pivot with respect to the block 20 about parallel or skewed axes of rotation. In other variations, the guide members 60 and 70 can be attached to the block 20 at different locations, such as on opposite ends 20A and 20B of block 20.

Depending on the location of where guide members 60 and 70 pivotably attach to block 20, separate bone cutting guides may be provided for left-side and right-side anatomies (e.g., a guide for a left foot and a guide for a right foot). In the embodiment shown in FIG. 1, the bone cutting guide 10 is configured for a left foot. In some embodiments, a bone cutting guide (or component thereof) is configured for a right foot and would be a minor image of the bone cutting guide 10 (or a component thereof, such as guide members 60 and/or 70) configured for a left foot. In other embodiments, such as that shown in FIGS. 3A and 3B, the bone cutting guide (or components thereof) is ambidextrous and can be configured for use on either foot. In some such embodiments, the guide members 60 and/or 70 can be detached from the block 20, turned over, and reattached to the block to work on the opposite foot. As shown, labeling can be provided to facilitate configuring the bone cutting guide (or component thereof) for either foot.

Figure 4:
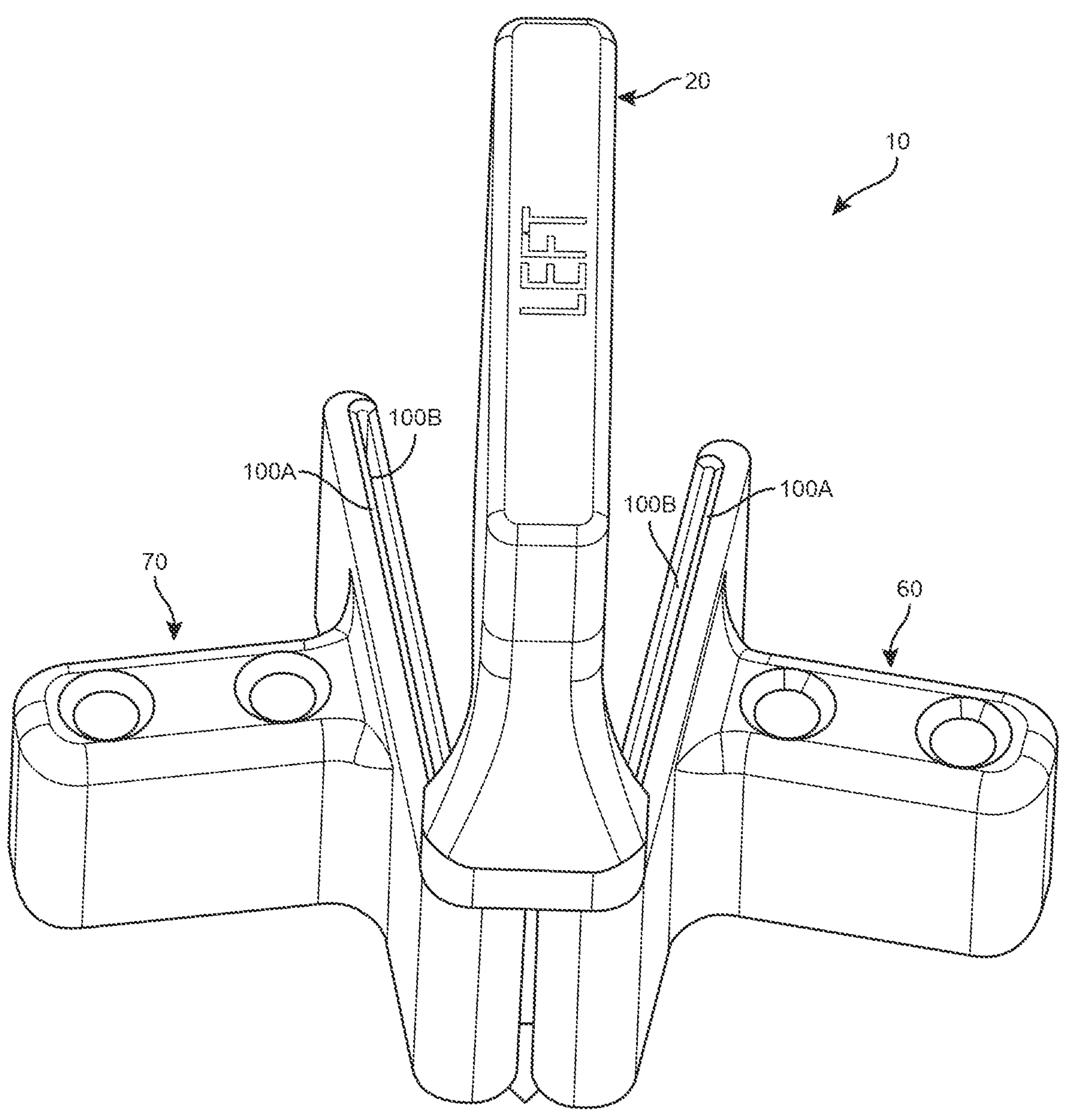
FIG. 4 is a perspective view of the bone cutting guide of FIG. 1 showing guide members of the bone cutting guide aligned at a skewed angle relative to a block of the bone cutting guide.

FIG. 4 illustrates a perspective view of the bone cutting guide 10 of FIGS. 1 and 2. In the illustrated embodiment, the guide members 60 and 70 are pivotally attached to the block 20. A location where a bone is to be cut can vary depending on the application of the bone cutting guide 10. In some applications, the guide member 60 and/or 70 can be aligned at the location to be cut by appropriately positioning the block 20 such that the first and/or second guide surfaces 100A and 100B, or a space defined between the guide surfaces 100A and 100B, is located at the location to be cut. For example, when performing a tarsal-metatarsal fusion procedure, block 20 may be positioned over a tarsal-metatarsal joint (e.g., with projection 50 inserted into the joint).

In some embodiments, it may be desirable to adjust the location of the guide member 60 and/or 70 relative to the block 20 so that the guide member 60 and/or 70 is aligned at the location desired to be cut. In the example shown in FIG. 4, the guide member 60 has been pivoted about the block 20 so that the guide member 60 is appropriately aligned at the location to be cut. Specifically, the guide member 60 has been pivoted about the block 20 so that the first guide surface 100A and the opening defined between the guide surfaces 100A and 100B is positioned at the location desired to be cut. Similarly, the guide member 70 has been aligned at a second location to be cut by pivoting the guide member 70 about the block 20 so that the guide surface 100A and the space defined between the guide surfaces 100A and 100B is positioned at the second location desired to be cut. Depending on the particular application, the guide members 60 and 70 can be pivoted about the block 20 to differing degrees. By pivotally attaching the guide member 60 and/or 70 to the block 20, bone cuts can be made at a wide range of locations. Further, because the projection 50 can be positioned within a joint, a longitudinal axis of the cut can be generally parallel with the projection while the plane of the cut can be angularly adjusted relative to the projection as desired.

Figure 5:
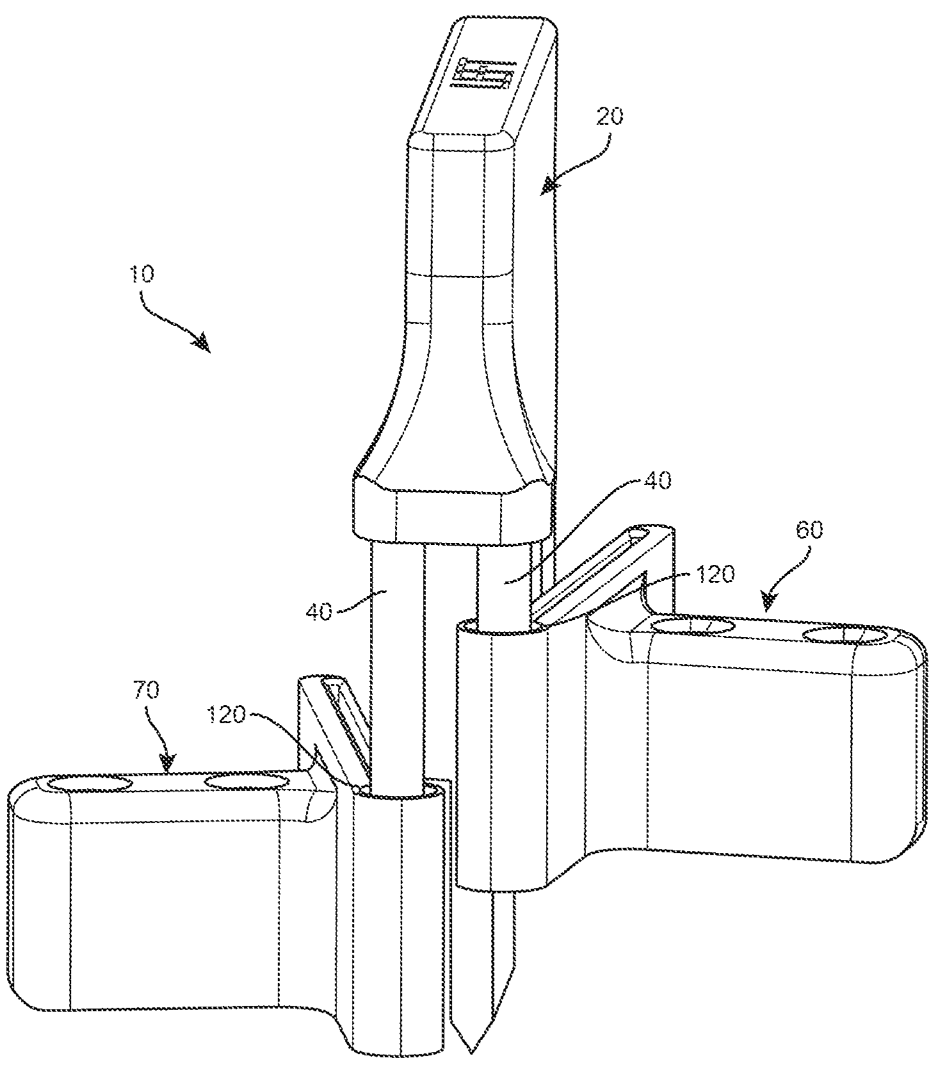
FIG. 5 is a perspective view of the bone cutting guide of FIG. 1 showing the guide members translated relative to a block of the bone cutting guide.

FIG. 5 shows a perspective view of the bone cutting guide 10 of FIGS. 1, 2, and 4. As described previously, the guide members 60 and 70 can be attached to the block 20 in a manner that allows the guide members 60 and 70 to translate with respect to the block 20, such as up and down along the respective guide attachment members 40. Configuring the guide members 60 and 70 to translate with respect to the block 20 allows the guide members 60 and 70 to be positioned at differing elevations, such as differing elevations along the attachment members 40. For instance, in the example shown in FIG. 5, the guide member 60 is at a higher elevation along its respective guide attachment member 40 relative to the guide member 70 along its respective guide attachment member 40. This can be beneficial, for example, where the block 20 is positioned between two bones having differing elevations (e.g., differing heights). In such an application, the guide members 60 and 70 can translate with respect to the block 20 (e.g. along the respective guide attachment members 40) so that each guide member 60 and 70 rests on the respective bone on each side of the block 20, even though the bone on each side of the block 20 is positioned at a different elevation.

Additionally, configuring the guide members 60 and 70 to translate with respect to the block 20 can allow the block 20 to be removed, for instance from a space defined between bones, while the guide members 60 and 70 remain in place. In the embodiment of the bone cutting guide 10 shown, the guide members 60 and 70 are free at an end opposite an end that can contact the block 20. When so configured, the block 20 may be pulled away from the guide members 60 and 70 without disturbing the guide members 60 and 70, which may provide more working room during a surgical procedure.

Figure 6A:
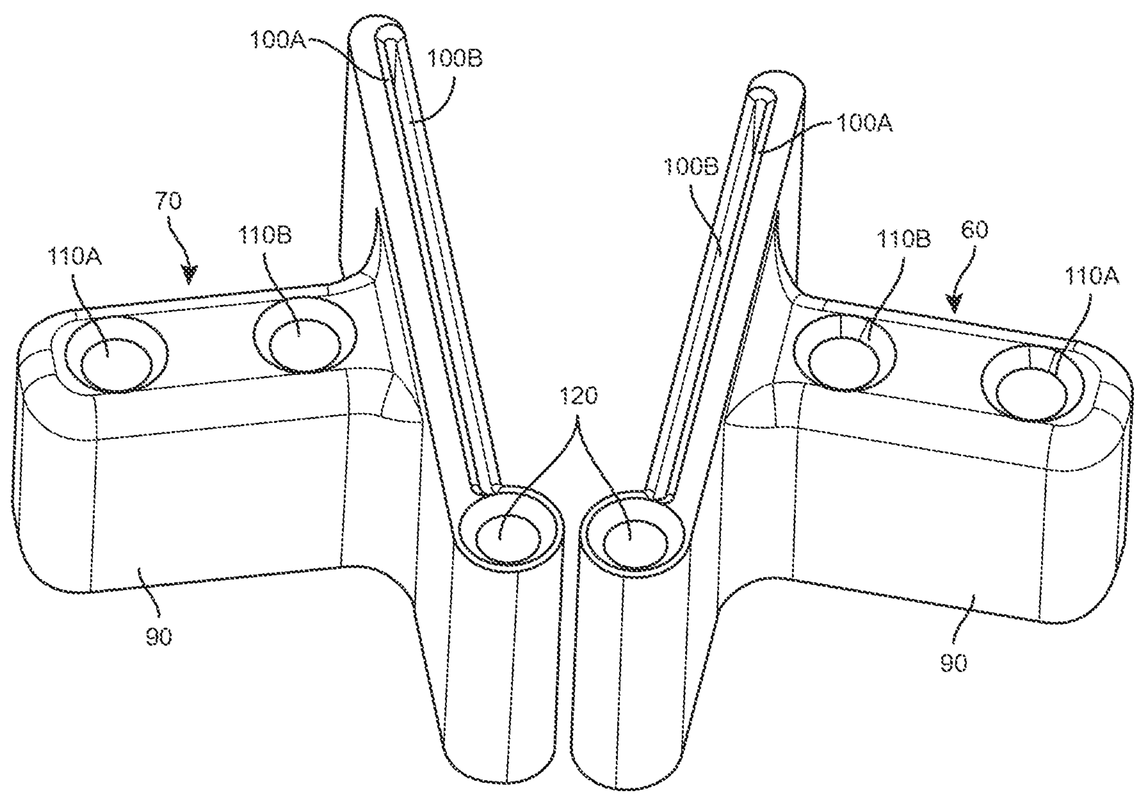
FIG. 6A is a perspective view showing the block of the bone cutting guide of FIG. 1 disconnected with the guide members of the bone cutting guide in place.
Figure 6B:
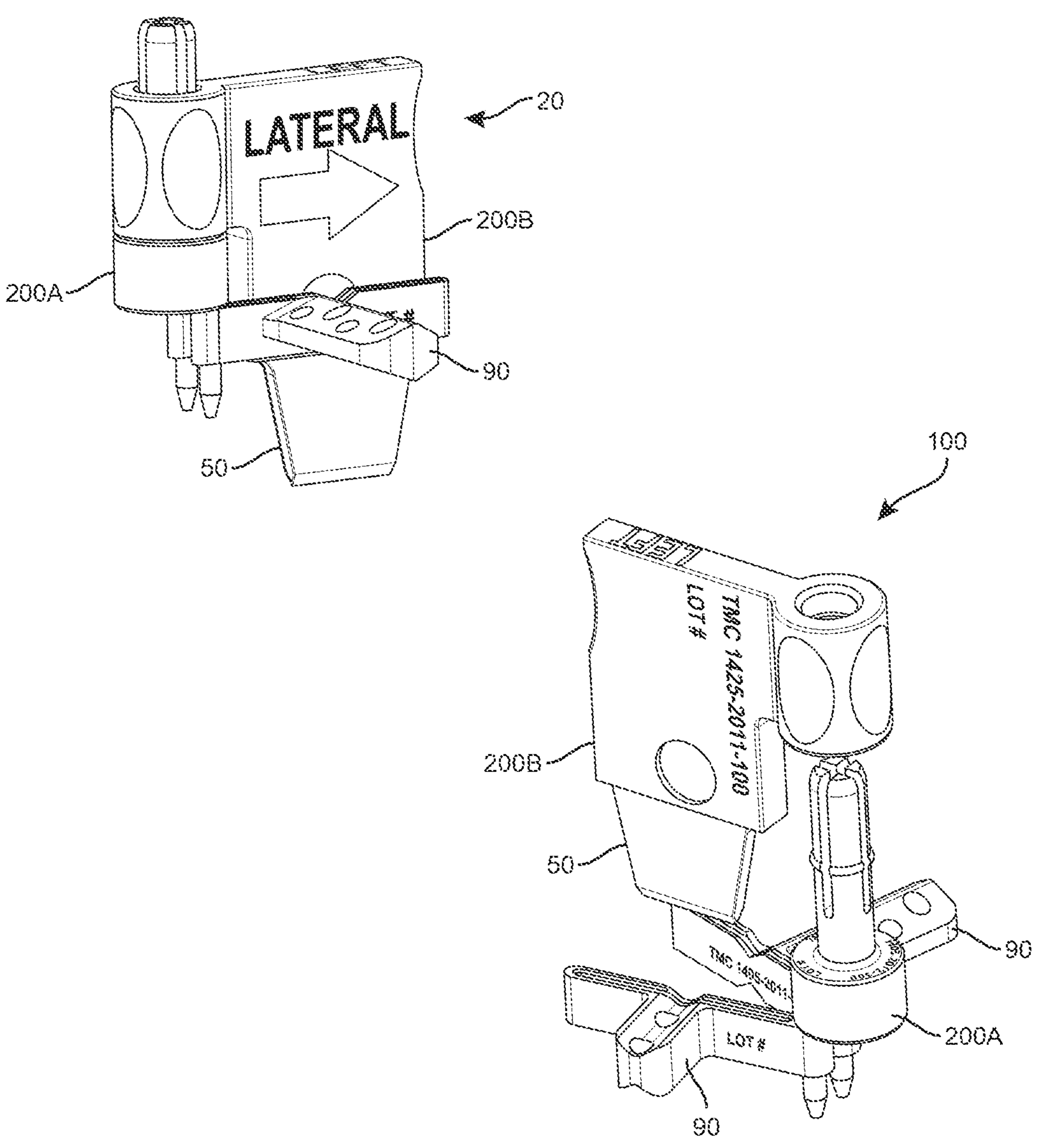
FIG. 6B is a perspective view of another embodiment of a bone cutting guide having a two portion block.

FIG. 6A shows the guide members 60 and 70 disconnected from the block 20. In some embodiments, such as the embodiment shown in FIG. 6B, the block 20 is configured such that a portion of it can be detached while leaving the guide members 60 and 70 coupled to the attachment members 40, which allows the guide members to remain coupled at any angle. In such embodiments, the block 20 has a first portion 200A connected to the attachment members 40 and a second portion 200B detachable from the first portion.

Figure 7:
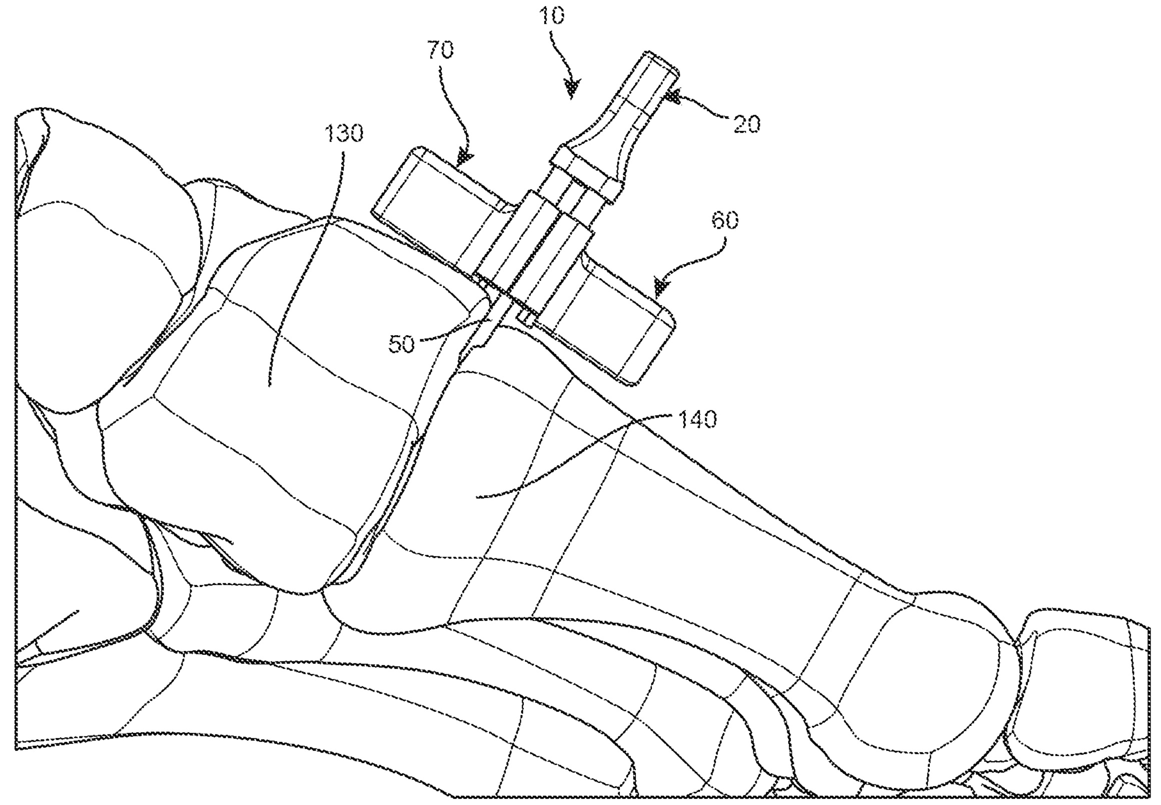
FIG. 7 is a side view showing the bone cutting guide of FIG. 1 positioned between bones.

FIG. 7 shows the bone cutting guide 10 positioned for use in cutting bones 130 and 140. In particular, FIG. 7 shows bone cutting guide 10 positioned on a tarsal-metatarsal joint with option projection 50 inserted into the joint. First guide member 60 in this example is positioned on first metatarsal 140 (e.g., to cut an end of the first metatarsal during a fusion procedure). Second guide member 70 in the example is positioned on medial cuneiform 130 (e.g., to cut an end of the medial cuneiform opposite the end of the first metatarsal being cut).

As shown, the bone cutting guide 10 can be positioned over and/or in a space defined between the bones 130 and 140. In particular, block 20 of bone cutting guide 10 can be positioned over and/or in a space defined between the bones 130 and 140. For embodiments where the block 20 includes the projection 50, the block 20 can be positioned at the space defined between the bones 130 and 140 such that the projection 50 extends into the space defined between the bones 130 and 140. The projection 50 can, for example, assist in positioning and spacing the bones 130 and 140.

The guide members 60 and 70 may each be aligned at respective locations on the bones 130 and 140 desired to be cut. For example, the guide members 60 and 70 may be rotated relative to block 20 until the first guide surface 110A and/or the second guide surface 100B of each guide member are positioned at respective locations on the bones 130 and 140 desired to be cut. In embodiments having guide surfaces 100A and 100B, the space defined between the guide surfaces 100A and 100B can be positioned at the respective locations on the bones 130 and 140 desired to be cut. Aligning the guide members 60 and 70 at the respective locations to be cut can include pivoting one or both guide members 60 and 70, for example at the apertures 120, about the block 20 as necessary. In addition, in some embodiments, aligning the guide member 60 and/or 70 can include translating the guide member 60 and/or 70 relative to and along the block 20 such that an elevation of the guide member 60 and/or 70 is adjusted, for instance, to match an elevation of the respective bone 130 and/or 140. The guide members 60 and 70 can be aligned such that cuts made to the bones 130 and 140 using the respective guide members 60 and 70 are parallel cuts. In other embodiments, the guide members 60 and 70 can be aligned such that the cuts made to the bones 130 and 140 are at non-parallel angles relative to each other.

Once the guide members 60 and/or 70 have been aligned at respective locations to be cut, the guide members 60 and/or 70 can be fixed to the respective bones 130 and 140. In the illustrated embodiment, bone fixation pins (FIG. 16) may be inserted through the fixation apertures 110A and/or 110B of the guide members 60 and/or 70 to fix the guide members 60 and/or 70 to the respective bones 130 and 140. An end of a bone fixation pin can be inserted through, for example, the fixation aperture 110B in the support 90 such that the end of the bone fixation pin is fixed to the respective bone 130 or 140.

After aligning and fixing the guide members 60 and/or 70, the block 20 may be removed from the space defined between the bones 130 and 140. The block 20 can be removed by pulling the block 20 away from the bones 130 and 140 in a direction opposite the bones 130 and 140. As such, in embodiments where the block 20 includes the projection 50, the projection 50 can also be removed from the space defined between the bones 130 and 140 by removing the block 20. In this manner, the block 20 can slide out from the guide members 60 and 70 while the guide members 60 and 70 remain fixed to the respective bones 130 and 140.

The bones 130 and 140 can be cut at the desired locations where the guide members 60 and/or 70 have been aligned. For example, a cutting member (e.g. a saw blade) can be placed in apposition (e.g., parallel and/or abutting arrangement) to the first guide surface 110A or, in some embodiments, inserted through the space defined between the first and second guide surfaces 100A and 100B to cut the respective bone 130 and/or 140. The guide surfaces 100A and 100B can serve to direct the cutting member to the location of the bone 130 or 140 to be cut, which in many applications of the bone cutting guide 10 can be a precise location.

When the bones 130 and/or 140 have been cut, the guide members 60 and/or 70 can be removed. Removing the guide members 60 and/or 70 may include removing any preparation fixation pins from the bones 130 and/or 140 as well as from the guide members 60 and/or 70. In some embodiments, the bones may then be compressed together and one or more bone plates may be applied.

Figure 8:
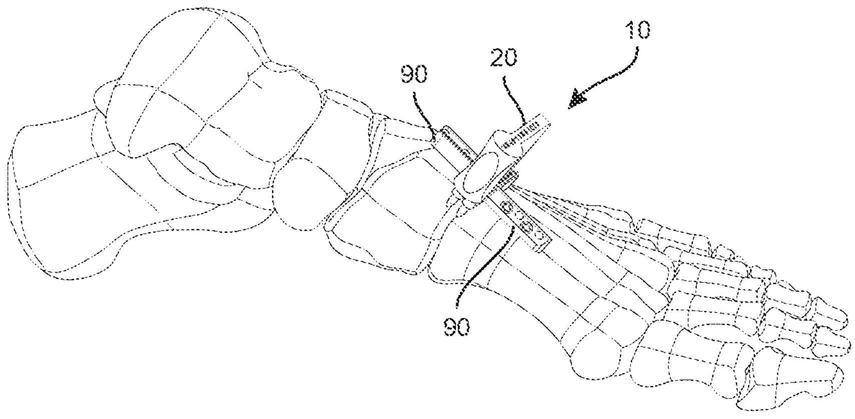
FIGS. 8-18 depict exemplary surgical methods and related components.

An exemplary method and related components will now be described with reference to FIGS. 8-18. As shown in FIG. 8, after making an incision, a cut guide (e.g., bone cutting guide 10 described with respect to FIGS. 1-7) can be placed into the incision. When configured with a projection, the projection can be inserted into a joint-space (e.g., metatarsal-cuneiform joint-space) to temporarily secure the guide in the joint. Further, inserting the projection of the block into the joint-space can be helpful to align the block and cutting surfaces with an anatomical axis of the bone to be cut. Such alignment may facilitate the proper placement of bone fixation pins for further positioning as described herein.

Figure 9:
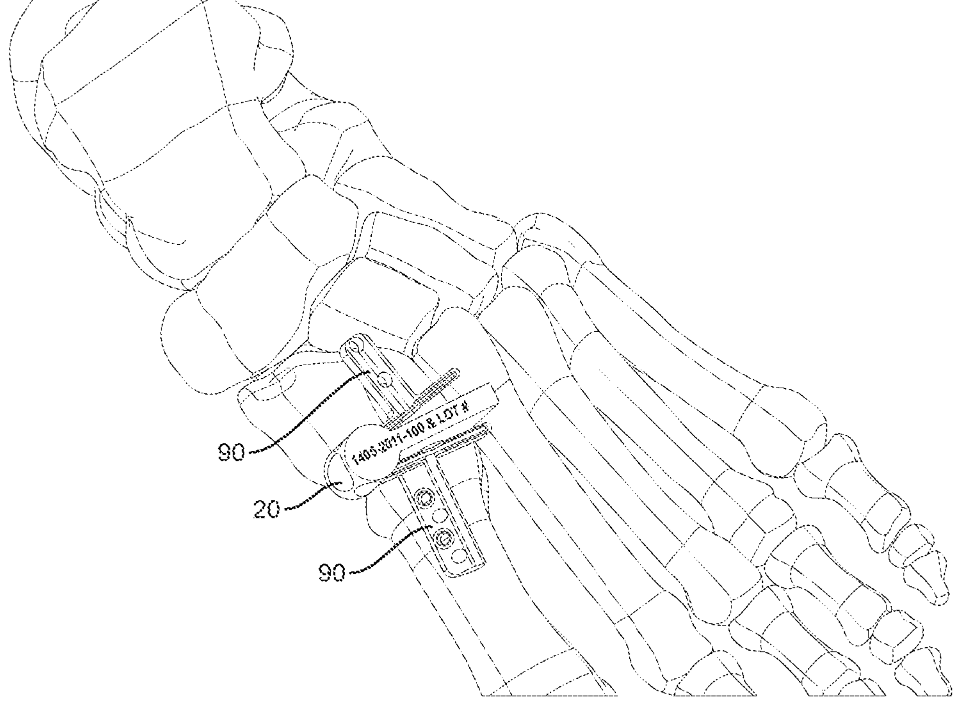

As shown in FIG. 9, a first guide member (e.g., the distal guide member) can be articulated with respect to the block to align it with a bone anatomic axis, such as the anatomic axis of a first metatarsal (e.g., the long or anterior-posterior axis of the bone). Before or after aligning the first guide member, a second guide member (e.g., the proximal guide member) can be articulated with respect to the block to align it with an axis of a second bone, such as a medial cuneiform (e.g., the long or anterior-posterior axis of the bone). Alignment may form an angle approximately equivalent to the angle of correction required for the patient's bone procedure.

Figure 10:
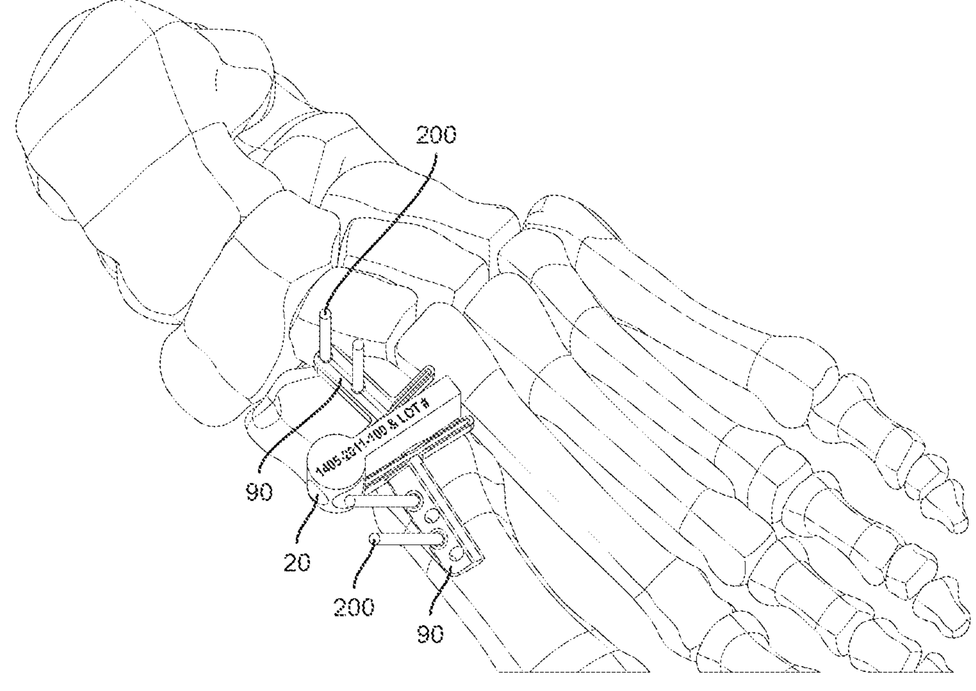

As shown in FIG. 10, one or more (e.g., two) bone preparation fixation pins 200 can be inserted into fixation apertures of the first guide member. Additionally, one or more (e.g., two) bone fixation pins can be inserted into the fixation apertures of the second guide member. In the embodiment shown, the fixation pins in the first guide member are inserted through fixation apertures at a skewed (e.g., 20 degree) angle relative to the fixation pins in the second guide member relative to a long axis of the bone. The pins can be parallel to each other to help determine any planar rotation about a central axis of the joint prior to or during fixation of the bones in their final position.

Figure 11:
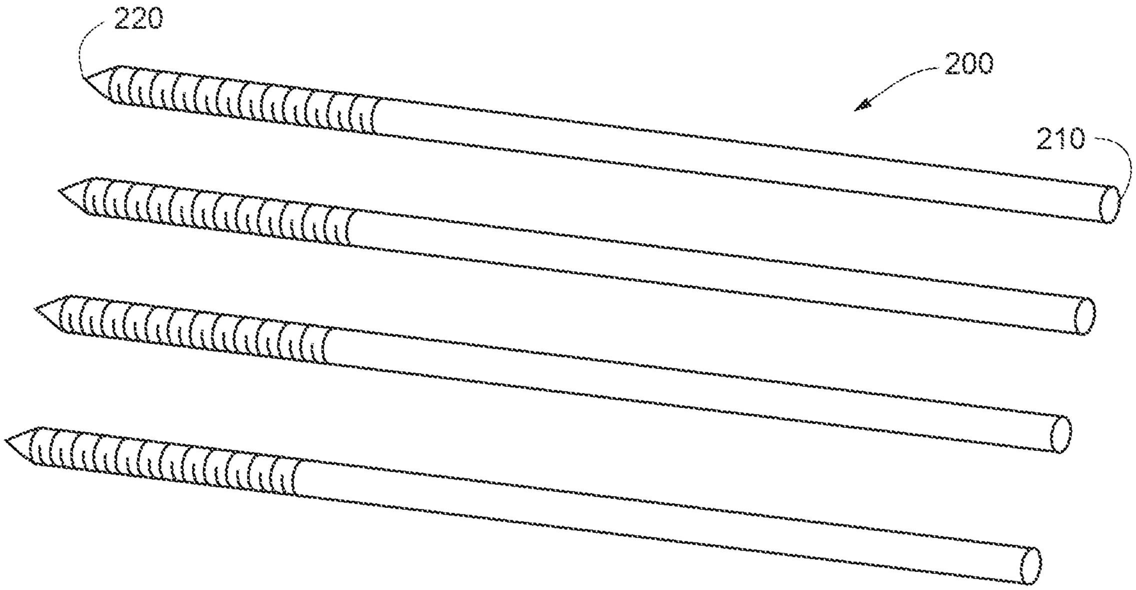

FIG. 11 illustrates a perspective view of an embodiment of bone preparation fixation pins 200. The bone preparation fixation pins include a first end 210 and a second end 220. The second end can be pointed and optionally threaded. As described herein, the bone preparation fixation pins can be used in to fixate a bone cutting guide to one or more bones and/or to provisionally position bones with respect to each other (e.g., rotationally, translationally, and/or elevationally) after removal of the guide and prior to installation of a bone plate.

Figure 12:
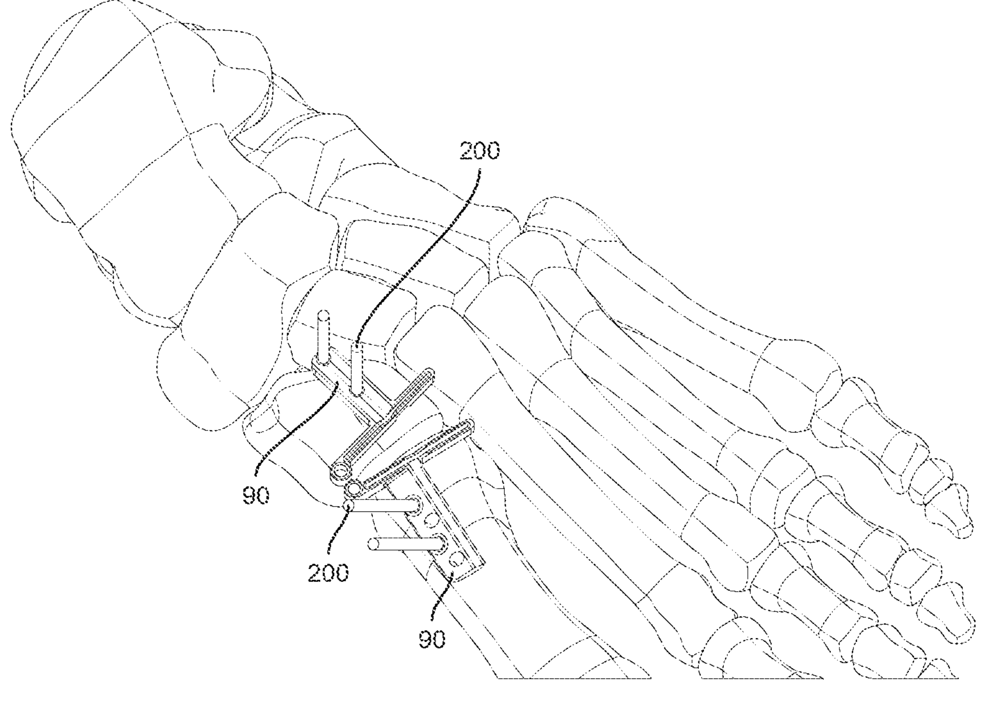

In FIG. 12, the block has been pulled out of the joint (vertically), uncoupling the guide members, which remain in place.

Figure 13:
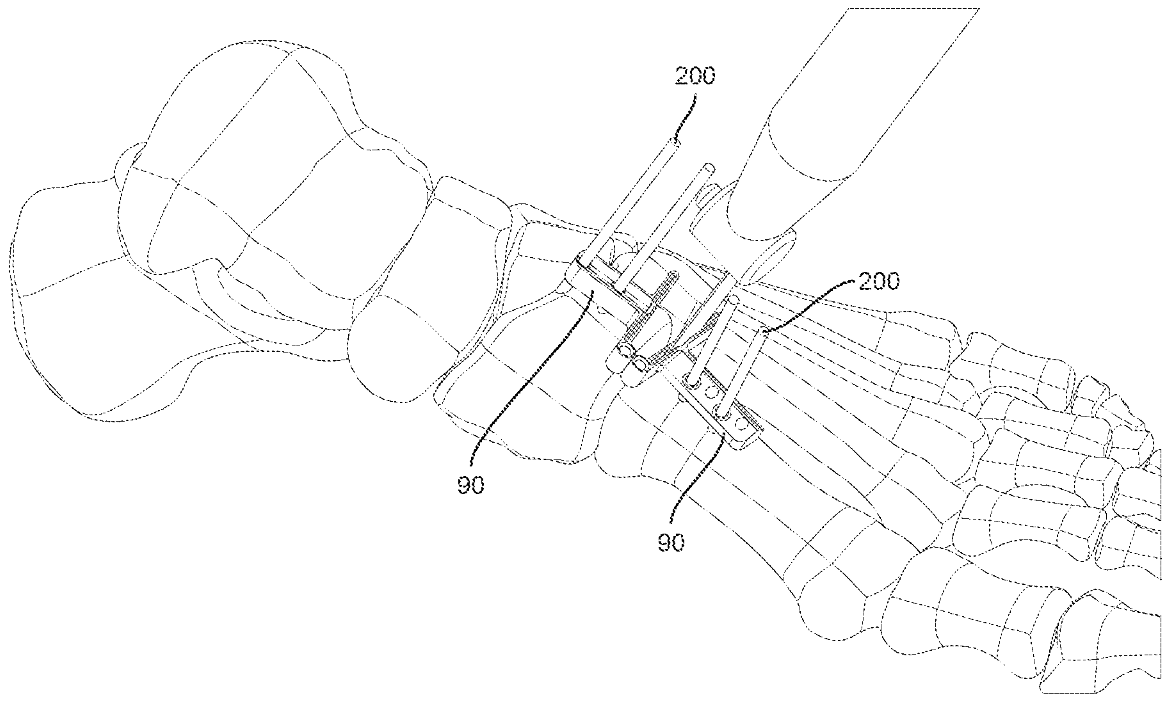

In FIG. 13, a cutting instrument (e.g., oscillating saw) is used to make the metatarsal cut through the cut slot on the first guide member. The cutting instrument can also be used to make the cut on the cuneiform through the cut slot on the second guide member.

Figure 14:
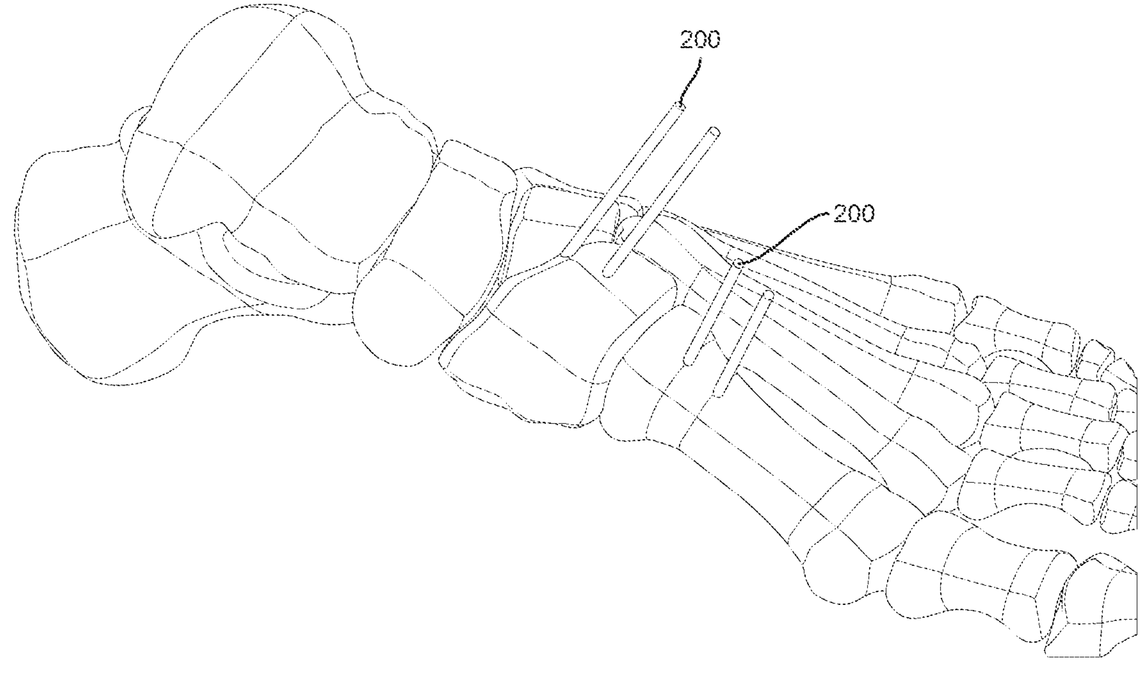

In FIG. 14, the guide members have been pulled vertically up and off of the pins. The cut bone pieces can then be removed.

Figure 15:
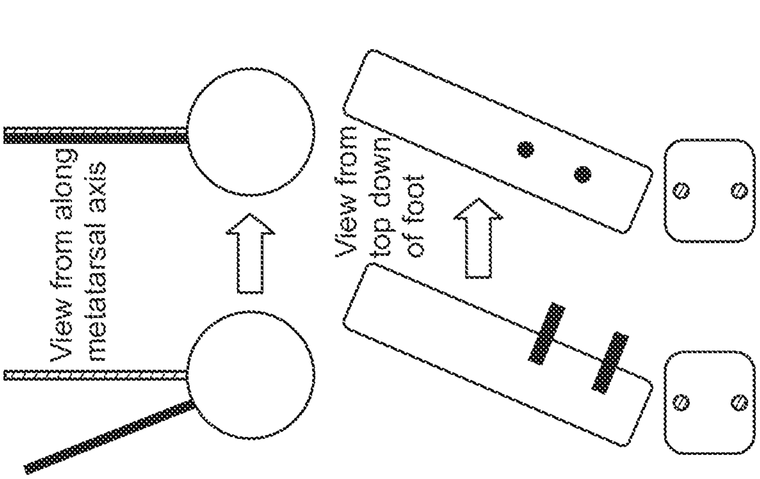
Figure 15:
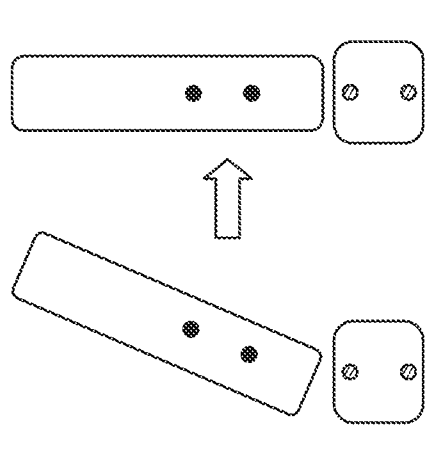

FIG. 15 shows schematic images that depict how the bone preparation fixation pins 200 can be used to align the bones with respect to each other. As shown, the pins can serve as a navigation tool for aligning one bone relative to the other in preparation for fusion. The pins can be used to move the first metatarsal from an anatomically misaligned position with respect to the second metatarsal to an anatomically aligned position with respect to the second metatarsal. For example, the first metatarsal may be moved in a frontal plane, transverse plane, and/or sagittal plane relative to the second metatarsal to move from an anatomically misaligned position to an anatomically aligned position. Additional details on bone alignment instruments and techniques that can be utilized in conjunction with the present disclosure are described in U.S. patent application Ser. No. 14/981,335, filed Dec. 28, 2015, and 62/293,189, filed Feb. 9, 2015, the entire contents of which are incorporated herein by reference.

In FIG. 14, the pins 200 may be used to rotate the distal bone in a frontal plane until the distal pins (inserted into the first metatarsal) are aligned with the proximal pins (inserted into the medial cuneiform) when the correction is complete. Having one or more pins on each bone can help guide the positioning of the bones in both rotation and translation. The pins can make it easier to manually manipulate the bones, serving as a "joystick." In some embodiments, the pins are an attachment point for a device to compress the joint in preparation for fusion. In some embodiments, a bone graft or other material is delivered to the joint site prior to compressing the bones and/or permanently fixating the joint.

Figure 16:
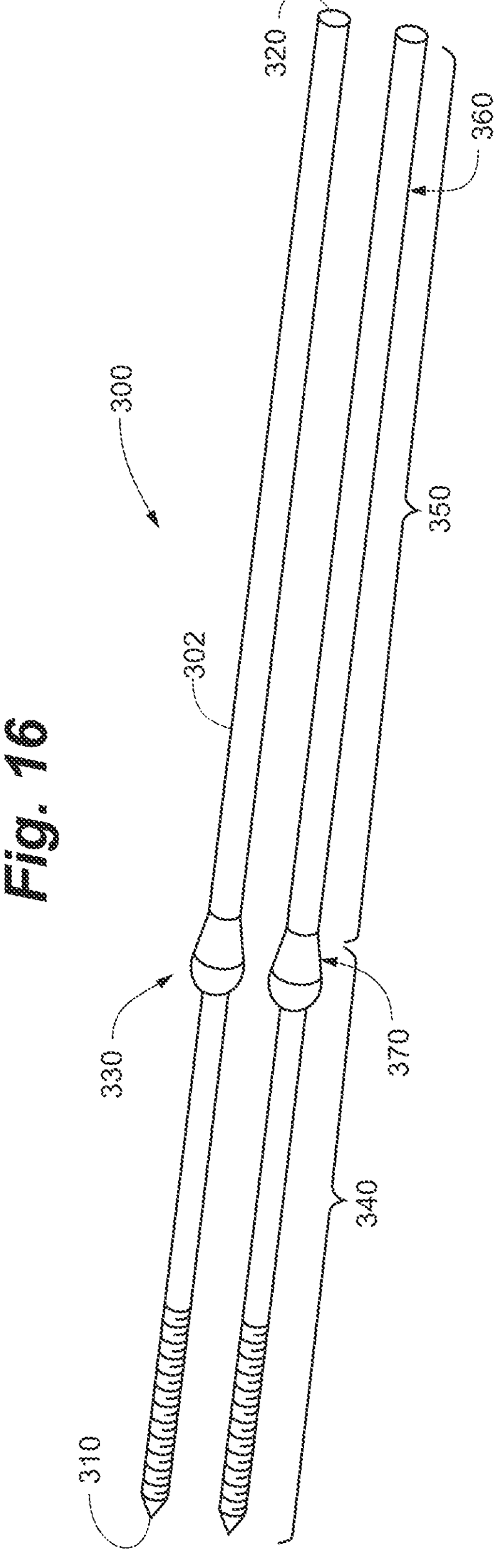

FIG. 16 shows a perspective view of an embodiment of a bone fixation pin that can be used to compress bones (e.g., a first metatarsal and medial cuneiform) together during a bone correction procedure. As shown, a bone fixation pin 300 includes a shaft 302 that has a first end 310 (which may be referred to as a distal or leading end) and a second end 320 (which may be referred to as a proximal or trailing end). The bone fixation pin 300 further includes a collar 330 (which may be referred to as an olive in some embodiments) positioned along the length of the shaft. The collar 330 may be a region of shaft 302 that has a larger cross-sectional dimension (e.g., diameter) than a remainder of the shaft. For example, the collar 330 may be a disc or cylinder shape, or bulbous or other shape, that projects outwardly away from a remainder of the shaft 302 (or at least a distal portion of the shaft that is intended to be inserted into bone).

Shaft 302 of bone fixation pin 300 may be threaded along at least a portion of its length. For example, shaft 302 may be threaded from first end 310 toward collar 330 along a portion of its length. In some examples, shaft 302 is threaded from the distal tip toward collar 330 at least 10% of the length of the shaft between the distal tip and distal edge of collar 330, such as from 10% of the length to 65% of the length. While fixation pin 300 can utilize a variety of different types of thread patterns, in some configurations, the threading provides a lag screw on the leading end of the bone fixation pin.

Depending on the particular application, bone fixation pin 300 may have a length ranging from 50 millimeters to 200 millimeters. Collar 330 in such examples may be positioned along the length of the shaft such that the distal edge of the collar ranges from about 20 mm to about 60 mm (e.g., 25 mm to 50 mm) from the distal-most tip of the pin, such as about 30 mm or about 40 mm. In some examples, collar 330 is positioned at a location effective to allow bone fixation pin 300 to be driven into and through one bone (e.g., a first metatarsal, medial cuneiform) and into but not through an adjacent bone (e.g., the other of the first metatarsal, medial cuneiform), with collar 330 being located to prevent the pin from being driven through the adjacent bone (e.g., by bearing against the first bone). Although the dimensions can vary, shaft 302 may have a diameter in the range of from 1.2 millimeters to 3.5 millimeters, outside of collar 330, while the collar may have a diameter ranging from 0.1 mm to 10 mm larger than the shaft.

Bone fixation pin 300 can be used to fix one or more bones in a particular position as desired for a surgical procedure. For example, at least one bone fixation pin 300 may be inserted into adjacent bones, crossing the joint space between the bones, and used to compress the bones together prior to the installation of a bone plate. For example, in some applications, adjacent bones are compressed by providing a bone fixation pin having a length, a threaded end portion, and a collar. The threaded end of the bone fixation pin may be driven into and through a first bone portion and into a second bone portion until the collar is in apposition to the first bone portion. The threaded end of the bone fixation pin may be further driven into the second bone portion to compress the first bone portion and the second bone portion together. In some embodiments, a second bone fixation pin is applied and used in the same manner. For example, the second bone fixation pin may be inserted through the second bone and into the first bone.

In different applications, the bone fixation pin(s) 300 can be removed after compressing the bone portions together or at least a portion of the bone fixation pin can be used as an implant that remains in the bone after completion of the surgical procedure. In one example configuration, bone fixation pin 300 is configured to be detachable proximally of collar 330, such as at a proximal edge of the collar. A proximal portion of bone fixation pin 300 may be detachable from a remainder of the pin by providing an area of weakened mechanical strength (e.g., area of reduced cross-section) configured to preferentially break or shear relative to a remainder of the pin. In some such configurations, fixation pin 300 may be sheared into an implantable portion that remains in the bone and a detachable and removable portion that is extracted from the patient. Fixation pin 300 may be sheared, for example, by increased torque or twisting force to the pin, causing the pin the cleave at the mechanically weakened area.

FIG. 16 further illustrates fixation pin 300 as having an optional implantable portion 340 and detachable portion 350, where a detachment region (e.g., mechanical weakening) is provided between the two portions. To drive fixation pin 300 into bone in such an example, the pin may have a main drive engagement surface 360, such as a surface on or adjacent the second end 320 that can be engaged with a mechanical driving instrument (e.g., drill, pliers). The fixation pin 300 may further have a secondary drive engagement surface 370 on or adjacent to (e.g., distal of) collar 330. Such secondary drive engagement surface can be engaged with the mechanical driving instrument after detachment of the implantable portion 340 from the detachable portion 350. This can be useful to further drive or remove the implantable portion into or from bone after detachment, if needed.

The bone fixation pins and the method described may be used in a surgical procedure along with a bone cutting guide, such as embodiments of the bone cutting guides described herein, or may be used independently of such guides. Further, in some embodiments, after driving the threaded end portion into the first bone portion and prior to driving the threaded end portion into the second bone portion, the position of the first bone portion can be adjusted (e.g., rotationally, translationally, and/or elevationally) relative to the position of the second bone portion by a manipulation of the bone fixation pin.

Figure 17B:
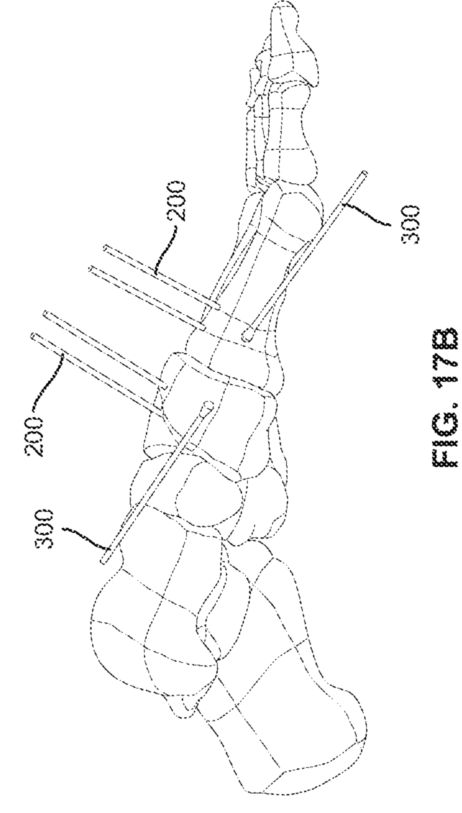
Figure 17A:
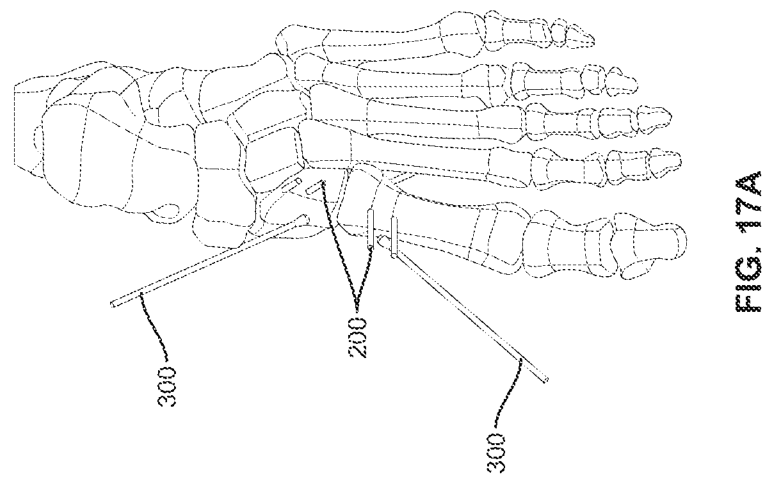

A specific embodiment is shown in FIGS. 17A and 17B. As shown, a bone fixation pin can be inserted from the metatarsal into the cuneiform, with a distal-medial to proximal-lateral trajectory, to compress the joint and provide provisional fixation of the alignment correction. A second bone fixation pin can be inserted from the cuneiform into the metatarsal, crisscrossing the first bone fixation pin for additional provisional fixation. In this example, the distal bone preparation fixation pins are still rotated in the frontal plane. However, they may be aligned and parallel with the proximal bone preparation fixation pins prior to the installation of the bone fixation pins. While FIGS. 17A and 17B show one example angular orientation of bone pins 300, other angular orientations can be used.

Figure 18:
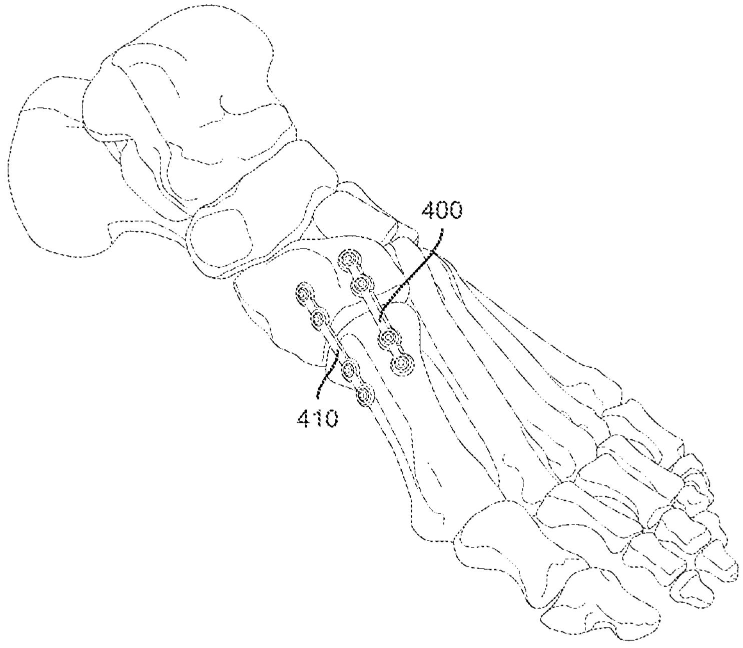

In FIG. 18, the four bone preparation fixation pins have been removed. A dorsal-medial bone plate 400 has been applied above (e.g., dorsally) the crossing bone fixation pins, and a plantar-medial bone plate 410 has been applied below (e.g., plantarly) the crossing bone fixation pins. For example, the two bone plates may be applied above and below the bone preparation fixation pins prior to removing the pins (e.g., such that the plates do not cover the holes created by the bone fixation pins) and the pins thereafter removed. In FIG. 18, the bone fixation pins are shown removed, e.g., after attachment of the bone plates. Additional details on example bone plates that can be used are described in U.S. patent application Ser. No. 14/990,368, filed Jan. 7, 2016, the entire contents of which are incorporated herein by reference.

Figure 19:
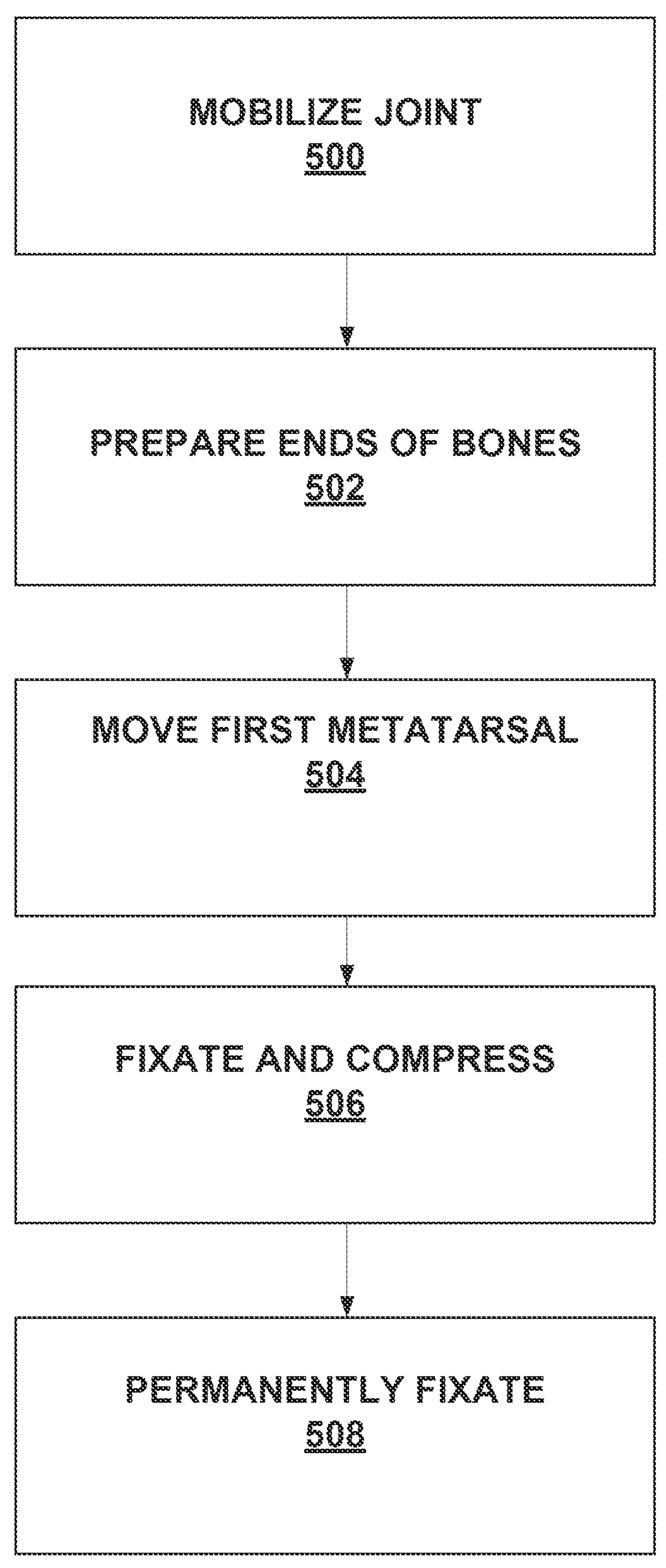
FIG. 19 is a block flow diagram of an example bone correction technique involving bone fixation pin compression that can be used in accordance with the disclosure.

FIG. 19 is a block flow diagram of an example bone correction technique involving bone fixation pin compression that can be used in accordance with the disclosure. Specific steps of the technique of FIG. 19 can be performed utilizing techniques and/or instruments discussed herein. As shown, the example technique of FIG. 19 includes mobilizing a tarsal-metatarsal joint by releasing soft tissue and/or obstructing bone (500). After customary surgical preparation and access, the clinician may mobilize the tarsal-metatarsal joint by inserting a cutting instrument (e.g., saw, rotary bur, osteotome) at least partially between the first metatarsal and medial cuneiform. The clinician may use the cutting instrument to release soft tissues and/or excise the plantar flare from the base of the first metatarsal. Excising the plantar flare may involve cutting plantar flare off the first metatarsal so the face of the first metatarsal is generally planar. In some applications, the dorsal-lateral flare of the first metatarsal may also be excised to create space for the correction procedure.

The technique of FIG. 19 further involves preparing the end of the first metatarsal and/or the opposed end of the medial cuneiform (502). To prepare the end of the first metatarsal and the end of the medial cuneiform, a tissue removing instrument can be applied to the ends of the bones. A bone cutting guide, such as bone cutting guide 10 having one or more rotatable guide members described herein, can be applied to the tarsal-metatarsal joint to guide the tissue removing instrument. As discussed, the one or more guide members of the bone cutting guide can be aligned to position a guide surface at the location on the bone where the tissue removal instrument is to be directed. Independent of whether a cutting guide is used or the specific configuration of the cutting guide, a cutting instrument may be applied to transect each bone and thereby form a new end surface, e.g., by inserting the cutting instrument along a guide surface and/or through a slot defined on by the guide. Additionally or alternatively, the tissue removing instrument can be applied to the end face of each bone to morselize at least a portion of the end face.

Independent of the specific technique used to prepare the end of the first metatarsal and/or the opposed end of the medial cuneiform (502), the technique of FIG. 19 includes moving the first metatarsal to help correct the anatomical misalignment (504). The first metatarsal can be moved relative to the second metatarsal before and/or after preparing the end of the first metatarsal and/or the opposed end of the medial cuneiform. In some applications, one or more provisional bone fixation pins are inserted into the first metatarsal and/or medial cuneiform (e.g., to attach bone cutting guide 10 at the tarsal-metatarsal joint) and used to guide alignment. For example, the clinician may grasp a provisional bone fixation pin inserted into a first metatarsal and used the pin to manipulate movement and realignment of the first metatarsal relative to the second metatarsal.

In some applications, the first metatarsal is moved from an anatomically misaligned position (e.g., characterized by a bunion deformity) to an anatomically aligned position. In some embodiments, an "anatomically aligned position" means that an angle of a long axis of a first metatarsal relative to a long axis of a second metatarsal is about 10 degrees or less in the transverse plane or sagittal plane. Depending on the application, anatomical misalignment can be corrected in both a transverse plane and a frontal plane. In the transverse plane, a normal intermetatarsal angle ("IMA") between a first metatarsal and a second metatarsal may be less than about 9 degrees (e.g., less than 6 degrees). An IMA of between about 6 degrees and about 13 degrees (e.g., between about 9 degrees and about 13 degrees) may be considered a mild or moderate misalignment of the first metatarsal relative to the second metatarsal. An IMA of greater than about 16 degrees may be considered a severe misalignment of the first metatarsal relative to the second metatarsal. In some embodiments, methods in accordance with the disclosure involve anatomically aligning the first metatarsal relative to the second metatarsal) by reducing the IMA from over 10 degrees to about 10 degrees or less (e.g., to an IMA of less than 6 degrees, such as to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, the method involves anatomically aligning the metatarsal by reducing the metatarsal rotation from about 4 degrees or more to less than 4 degrees (e.g., to about 0 to 2 degrees) by rotating the metatarsal with respect to the medial cuneiform.

Thus, in some applications of the technique of FIG. 19, the clinician moves the first metatarsal in at least one plane from an anatomically misaligned position with respect to the second metatarsal to an anatomically aligned position. The at least one plane may be one or more planes selected from the frontal plane, the transverse plane, and the sagittal plane. For example, the clinician may move the first metatarsal in any two of the three planes or even in all three of the planes to adjust the first metatarsal from an anatomically misaligned position to an anatomically aligned position. Rotating the first metatarsal in the frontal plane may further rotate the sesamoid bones (e.g., tibial sesamoid bone and fibular sesamoid bone) from a misaligned position to an aligned position under the first metatarsal.

After suitably moving the first metatarsal relative to the second metatarsal, the joint between the first metatarsal and medial cuneiform may be provisionally fixated and the first metatarsal and medial cuneiform compressed together (506). To provisionally fixate and compress the bones together, a bone fixation pin may be driven into one of the first metatarsal and the medial cuneiform. When the bone fixation pin is configured with a threaded leading end, the leading end may be threadingly advanced into one of the bones (e.g., by rotating and drilling the pin into the bone). Alternatively, the bone fixation pin may be hammered into the bone. In either case, the bone fixation pin may be advanced completely through a cross-section of the bone until the pin emerges on a generally opposite side of the bone. The fixation pin may be further advanced through the bone until the leading end of the pin contacts the other bone (either the medial cuneiform or first metatarsal). The fixation pin may thereafter continue to be driven through the first bone and into the second bone until the collar on the pin presses against the bone the pin is inserted through. The collar may prevent the pin from advancing farther through the first bone and, correspondingly, into the second bone (until the first bone is itself moved closed to the second bone).

In some applications of the technique, the space between the first metatarsal and medial cuneiform (e.g., tarsal-metatarsal joint) is compressed by continuing to drive the bone fixation pin in the bones. As the pin is driven into the bone structure, the collar can bear and press against an outer surface of the first bone, pushing the first bone into contact with the second bone and thereby compressing the bones together. The amount of compression can be controlled by controlling the depth the fixation pin is driven into the second bone. In addition to compressing the bones together, the bone fixation pin can provisionally fixate, or hold, the bones in alignment together (e.g., until permanent fixation).

In different applications of the technique of FIG. 19, one or more bone fixation pins are inserted into the first metatarsal and the medial cuneiform to compress the bones together. In one example, one bone fixation pin is inserted into and through the first metatarsal and further into the medial cuneiform. In addition, a second bone fixation pin is inserted into and through the medial cuneiform and further into the first metatarsal. Both bone fixation pins are then driven (e.g., sequentially) toward the tarsal-metatarsal joint to bi-directionally compress the bones together.

Following compression, the corrected position of the first metatarsal can be permanently fixated by fixing the position of the first metatarsal with respect to the medial cuneiform (508). In some examples, permanent fixation involves detaching an implantable portion of the one or more bone fixation pins inserted into the first metatarsal and medial cuneiform from a remaining portion of the pins. Additionally or alternatively, one or more bone plates can be applied across the tarsal-metatarsal joint and the provisional bone fixation pins removed. For example, a first bone plate may be positioned on a dorsal-medial region of the first metatarsal and on the medial cuneiform while a second bone plate is positioned on a medial-plantar region of the first metatarsal and on the medial cuneiform. In these applications, the second bone plate may or may not be a helical-shaped bone plate extending from a medial region of the medial cuneiform to a plantar region of the first metatarsal across the joint.

Thus, embodiments of the invention are disclosed. Although the present invention has been described with reference to certain disclosed embodiments, the disclosed embodiments are presented for purposes of illustration, and not limitation, and other embodiments of the invention are possible. One skilled in the art will appreciate that various changes, adaptations, and modifications may be made without departing from the spirit of the invention.

The invention claimed is:

1. A method of performing a bunion correction procedure, the method comprising:

inserting a projection extending downwardly from and attached to a first cutting guide member into a tarsal-metatarsal joint between a first metatarsal and a medial cuneiform and positioning a first cut slot defined by the first cutting guide member at a location over the first metatarsal to be cut;

guiding a cutting instrument through the first cut slot to cut the first metatarsal;

moving the first metatarsal in a transverse plane and in a frontal plane to correct a bunion deformity;

positioning a second cut slot defined by a second cutting guide member at a location over the medial cuneiform to be cut, wherein the second cutting guide member is physically separate from the first cutting guide member;

guiding the cutting instrument through the second cut slot to cut the medial cuneiform, wherein guiding the cutting instrument through the first cut slot to cut the first metatarsal and guiding the cutting instrument through the second cut slot to cut the medial cuneiform comprises cutting an end of the medial cuneiform to be skewed relative to an end of the first metatarsal;

compressing the end of the first metatarsal together with the end of the medial cuneiform; and permanently fixating a position of the first metatarsal with respect to the medial cuneiform.

2. The method of claim 1, further comprising morselizing an end face of the first metatarsal and morselizing an end face of the medial cuneiform.

3. The method of claim 1, further comprising moving the first metatarsal in a sagittal plane to correct the bunion deformity.

4. The method of claim 1, wherein moving the first metatarsal in the frontal plane comprises rotating sesamoid bones from a misaligned position to an aligned position under the first metatarsal.

5. The method of claim 1, wherein:

guiding the cutting instrument through the first cut slot to cut the first metatarsal comprises guiding the cutting instrument through the first cut slot to cut the first metatarsal before moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

6. The method of claim 1, wherein:

guiding the cutting instrument through the first cut slot to cut the first metatarsal comprises guiding the cutting instrument through the first cut slot to cut the first metatarsal after moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

7. The method of claim 1, wherein permanently fixating the position of the first metatarsal with respect to the medial cuneiform inserting a fixation pin into the first metatarsal and the medial cuneiform and/or applying a bone plate to the first metatarsal and the medial cuneiform across the tarsal-metatarsal joint.

8. The method of claim 1, further comprising, prior to permanently fixating the position of the first metatarsal with respect to the medial cuneiform, provisionally fixating the position of the first metatarsal with respect to the medial cuneiform.

9. A method of performing a bunion correction procedure, the method comprising:

inserting a projection extending downwardly from and attached to a first cutting guide member into a tarsal-metatarsal joint between a first metatarsal and a medial cuneiform and positioning a first cut slot defined by the first cutting guide member at a location over the first metatarsal to be cut by at least aligning a support body of the first cutting guide member with a longitudinal axis of the first metatarsal, wherein the support body comprises two parallel fixation apertures and one skewed fixation aperture;

inserting two fixation pins through the two parallel fixation apertures of the support body and one fixation pin through the one skewed aperture of the fixation body;

after inserting the two fixation pins through the two parallel fixation apertures of the support body and one fixation pin through the one skewed aperture of the fixation body, guiding a cutting instrument through the first cut slot to cut the first metatarsal;

moving the first metatarsal in a transverse plane and in a frontal plane to correct a bunion deformity;

positioning a second cut slot defined by a second cutting guide member at a location over the medial cuneiform to be cut, wherein the second cutting guide member is physically separate from the first cutting guide member;

guiding the cutting instrument through the second cut slot to cut the medial cuneiform;

compressing an end of the first metatarsal together with an end of the medial cuneiform; and permanently fixating a position of the first metatarsal with respect to the medial cuneiform.

10. The method of claim 9, further comprising morselizing an end face of the first metatarsal and morselizing an end face of the medial cuneiform.

11. The method of claim 9, further comprising moving the first metatarsal in a sagittal plane to correct the bunion deformity.

12. The method of claim 9, wherein moving the first metatarsal in the frontal plane comprises rotating sesamoid bones from a misaligned position to an aligned position under the first metatarsal.

13. The method of claim 9, wherein the support body is linear and extends perpendicularly from the first cut slot and generally parallel to the longitudinal axis of the first metatarsal.

14. The method of claim 9, wherein positioning the second cut slot defined by the second cutting guide member at the location over the medial cuneiform to be cut comprises aligning a support body of the second cutting guide member with a longitudinal axis of the medial cuneiform.

15. The method of claim 14, wherein the support body is linear and extends perpendicularly from the second cut slot and generally parallel to the longitudinal axis of the medial cuneiform.

16. The method of claim 9, wherein:

guiding the cutting instrument through the first cut slot to cut the first metatarsal comprises guiding the cutting instrument through the first cut slot to cut the first metatarsal before moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

17. The method of claim 9, wherein:

guiding the cutting instrument through the first cut slot to cut the first metatarsal comprises guiding the cutting instrument through the first cut slot to cut the first metatarsal after moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

18. The method of claim 9, wherein guiding the cutting instrument through the first cut slot to cut the first metatarsal and guiding the cutting instrument through the second cut slot to cut the medial cuneiform comprises cutting the end of the medial cuneiform to be parallel to the end of the first metatarsal.

19. The method of claim 9, wherein guiding the cutting instrument through the first cut slot to cut the first metatarsal and guiding the cutting instrument through the second cut slot to cut the medial cuneiform comprises cutting the end of the medial cuneiform to be skewed relative to the end of the first metatarsal.

20. The method of claim 9, wherein permanently fixating the position of the first metatarsal with respect to the medial cuneiform inserting a fixation pin into the first metatarsal and the medial cuneiform and/or applying a bone plate to the first metatarsal and the medial cuneiform across the tarsal-metatarsal joint.

21. A method of performing a bunion correction procedure, the method comprising:

inserting a projection extending downwardly from and attached to a first cutting guide member into a tarsal-metatarsal joint between a first metatarsal and a medial cuneiform and positioning a first cut slot defined by the first cutting guide member at a location over the first metatarsal to be cut;

guiding a cutting instrument through the first cut slot to cut the first metatarsal;

moving the first metatarsal in a transverse plane and in a frontal plane to correct a bunion deformity;

positioning a second cut slot defined by a second cutting guide member at a location over the medial cuneiform to be cut by at least aligning a support body of the second cutting guide member with a longitudinal axis of the medial cuneiform, wherein the second cutting guide member is physically separate from the first cutting guide member;

guiding the cutting instrument through the second cut slot to cut the medial cuneiform;

compressing an end of the first metatarsal together with an end of the medial cuneiform; and permanently fixating a position of the first metatarsal with respect to the medial cuneiform.

22. The method of claim 21, further comprising morselizing an end face of the first metatarsal and morselizing an end face of the medial cuneiform.

23. The method of claim 21, further comprising moving the first metatarsal in a sagittal plane to correct the bunion deformity.

24. The method of claim 21, wherein the support body is linear and extends perpendicularly from the second cut slot and generally parallel to the longitudinal axis of the medial cuneiform.

25. The method of claim 21, wherein the support body comprises a fixation aperture, and further comprising inserting a fixation pin through the fixation aperture and into the medial cuneiform prior to guiding the cutting instrument through the second cut slot to cut the medial cuneiform.

26. The method of claim 21, wherein:

guiding the cutting instrument through the first cut slot to cut the first metatarsal comprises guiding the cutting instrument through the first cut slot to cut the first metatarsal before moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

27. The method of claim 21, wherein:

guiding the cutting instrument through the first cut slot to cut the first metatarsal comprises guiding the cutting instrument through the first cut slot to cut the first metatarsal after moving the first metatarsal in the transverse plane and in the frontal plane to correct the bunion deformity; and guiding the cutting instrument through the second cut slot to cut the medial cuneiform comprises guiding the cutting instrument through the second cut slot to cut the medial cuneiform after moving the first metatarsal in the transverse plane and in the frontal plane to correct the bunion deformity.

28. The method of claim 21, wherein guiding the cutting instrument through the first cut slot to cut the first metatarsal and guiding the cutting instrument through the second cut slot to cut the medial cuneiform comprises cutting the end of the medial cuneiform to be parallel to the end of the first metatarsal.

29. The method of claim 21, wherein guiding the cutting instrument through the first cut slot to cut the first metatarsal and guiding the cutting instrument through the second cut slot to cut the medial cuneiform comprises cutting the end of the medial cuneiform to be skewed relative to the end of the first metatarsal.

30. The method of claim 21, wherein permanently fixating the position of the first metatarsal with respect to the medial cuneiform inserting a fixation pin into the first metatarsal and the medial cuneiform and/or applying a bone plate to the first metatarsal and the medial cuneiform across the tarsal-metatarsal joint.

* * * * *